US007906103B2

(12) United States Patent
Graupner

(10) Patent No.: US 7,906,103 B2
(45) Date of Patent: Mar. 15, 2011

(54) METHODS AND COMPOSITIONS FOR TARGETED DRUG DELIVERY

(76) Inventor: Gerhard Graupner, San Diego, CA (US)

( * ) Notice: Subject to any disclaimer, the term of this patent is extended or adjusted under 35 U.S.C. 154(b) by 1146 days.

(21) Appl. No.: 11/549,832

(22) Filed: Oct. 16, 2006

(65) Prior Publication Data

US 2007/0203332 A1 Aug. 30, 2007

Related U.S. Application Data

(63) Continuation-in-part of application No. 10/238,755, filed on Sep. 9, 2002, now Pat. No. 7,122,172, and a continuation-in-part of application No. 09/936,094, filed on Mar. 14, 2002, now abandoned, which is a continuation of application No. PCT/US00/06001, filed on Mar. 8, 2000.

(60) Provisional application No. 60/318,270, filed on Sep. 7, 2001.

(51) Int. Cl.
*A61K 51/00* (2006.01)
*A61M 36/14* (2006.01)

(52) U.S. Cl. ............... 424/1.73; 424/1.11; 424/1.65; 424/1.69; 424/9.1; 514/9

(58) Field of Classification Search ............... 424/1.11, 424/1.65, 1.69, 1.73, 9.1, 9.2; 530/300, 326, 530/327, 333, 338, 350; 536/22.1, 23.1; 514/743, 806, 9, 44
See application file for complete search history.

(56) References Cited

U.S. PATENT DOCUMENTS

| | | | |
|---|---|---|---|
| 5,650,134 A | 7/1997 | Albert et al. | |
| 5,670,320 A | 9/1997 | Wallace et al. | |
| 5,686,261 A | 11/1997 | Zhang et al. | |
| 5,846,741 A | 12/1998 | Griffiths et al. | |
| 5,976,496 A | 11/1999 | Dean et al. | |
| 6,020,192 A | 2/2000 | Muzyczka | |
| 6,074,625 A | 6/2000 | Hawthorne et al. | |
| 6,080,728 A | 6/2000 | Mixson | |
| 6,171,859 B1 | 1/2001 | Herrnstadt et al. | |
| 6,225,284 B1 | 5/2001 | Albert et al. | |
| 6,242,381 B1 | 6/2001 | Van der Krieken | |
| 6,245,531 B1 | 6/2001 | Hogness et al. | |
| 6,248,305 B1 | 6/2001 | Groziak | |
| 6,316,652 B1 | 11/2001 | Steliou | |
| 6,333,318 B1 | 12/2001 | Evans et al. | |
| 6,432,915 B1 | 8/2002 | Bandman et al. | |
| 7,122,172 B1 * | 10/2006 | Graupner | 424/9.42 |

OTHER PUBLICATIONS

Barth Rolf F.et al., "Enhanced Delivery of Boronophenylalanine for Neutron Capture Therapy of Brain Tumors Using the Bradykinin Analog Cereport (Receptor-Mediated Permeabilizer-7)", Neurosurgery, vol. 44, No. 2, Feb. 1999, pp. 351-360.

Dennie, Joelle et al., "NMR Imaging of Changes in Vascular Morphology Due to Tumor Angiogenesis", MGH-NMR Center, Dept of Radiology, Jul. 1998, pp. 793-799.
Weissleder, Ralph et al., "In Vivo Magnetic Resonance Imaging of Transgene Expression", Nature Medicine, vol. 6, No. 3, Mar. 2000, pp. 351-354.
Reddy, Alyssa T. et al., "Pediatric Central Nervous System Tumors",Current Opinion in Oncology, 1998, pp. 183-193, Lippincott-Raven.
Hurt, Eduard C. et al., "The Cleavable Prepiece of an Imported Mitochondrial Protein is Sufficient to Direct Cytosolic Dihydrofolate Reductase into the Mitochondrial Matrix", Federation of European Biochemical Societies, vol. 178, No. 2, pp. 306-310.
McGarvey, Megan E. et al., "Emerging Treatments for Epidemic (AIDS-related) Kaposi's Sarcoma", Current Opinion in Oncology, 1998, pp. 413-421.
Smith, Robin A.J. et al., "Selective Targeting of an Antioxidant to Mitochondria", European Journal of Biochemistry, vol. 263, 1999, pp. 709-716.
Dingwall, Colin et al., "Nuclear Targeting Sequences—a Consensus?", TIBS 16, Dec. 1991, pp. 478-481, Elsevier Science Publishers (UK).
Grandchamp, Bernard et al., "Molecular Hepatology, Review: Molecular Pathogenesis of Hepatic Acute Porphyrias", Journal of Gastroenterology and Hepatology, vol. 11, 1996, pp. 1046-1052.
Balistreri, William F., MD, "Inborn Errors of Bile Acid Biosynthesis and Transport, Novel Forms of Metabolic Liver Disease", Gastroenterology Clinics of North America, vol. 28, No. 1, Mar. 1999, pp. 145-172.
Cox, Diane W., "Disorders of Copper Transport", British Medical Bulletin, 1999, 55 (No. 3), pp. 544-555.
Tracy Jr., Thomas F. et al., "Molecular and Cellular Control Points in Pediatric Liver Injury and Repair", Seminars in Pediatric Surgery, vol. 5, No. 3 (Aug. 1996), pp. 175-181.
Hartl, Franz-Ulrich et al., "Protein Sorting to Mitochondria: Evolutionary Conservations of Folding and Assembly", Science, vol. 247, Feb. 1990, pp. 930-993.
Pfanner, Nikolaus et al., "Mitochondrial Preprotein Translocase", Ann. Rev. Cell Dev. Biol., 1997, 13, pp. 25-511.
Cahill, MR et al., "Haemophilia", Postgrad Med Journal, 1996, pp. 201-206.
Felipo, Vicente et al., "Mitochondrial Dysfunction in Acute Hyperammonemia", Neurochemistry International 40, 2002, pp. 487-491.
Treem, William R., M.D. et al., "Disorders of the Mitochondria", Seminars in Liver Disease, vol. 18, No. 3, 1998, pp. 237-253.
Bakker, Henk D. et al., "Depletion of Mitochondrial Deoxyribonucleic Acid in a Family with Fatal Neonatal Liver Disease", The Journal of Pediatrics, vol. 128, No. 5, Part 1, pp. 683-687.
Mazzella, M et al., "Severe Complex I Deficiency in a Case of Neonatal-Onset Lactic Acidosis and Fatal Liver Failure", Acta Paediatr 86, 1997, pp. 326-329.

(Continued)

*Primary Examiner* — D L Jones
(74) *Attorney, Agent, or Firm* — Fitch, Even, Tabin & Flannery

(57) ABSTRACT

Disclosed are Drug Delivery Molecules (DDMs) which both facilitate functional imaging, as by PET, MRI or SPECT, and create a biological effect and methods of their use. These DDMs which are variously designed to target specific receptors, internalized and then function biologically, as for purposes of cell destruction or therapy.

19 Claims, No Drawings

OTHER PUBLICATIONS

Yanagie, H et al., Inhibition of Human Pancreatic Cancer Growth in Nude Mice by Boron Neutron Capture Therapy, British Journal of Cancer, 75(5), 1997, pp. 660-665.

O'Donoghue, Joseph A., "Strategies for Selective Targeting of Auger Electron Emitters to Tumor Cells", The Journal of Nuclear Medicine, vol. 37, No. 4 (Suppl), Apr. 1996, pp. 3S-6S.

Dwenson, David. H. et al., "Synthesis and Evaluation of a Boronated Nitroimidazole for Boron Neutron Capture Therapy", J. Med. Chem, 1996, 39, pp. 1540-154.

Nguyen, Tien et al., "Intracellular Distribution of Various Boron Compounds for Use in Boron Neutron Capture Therapy", Biochemical Pharmacology, vol. 45, No. 1, 1993, pp. 147-155.

* cited by examiner

METHODS AND COMPOSITIONS FOR TARGETED DRUG DELIVERY

This application is a continuation-in-part of Ser. No. 10/238,755, filed Sep. 9, 2002, which claims priority from U.S. Provisional Application Ser. No. 60/318,270, filed on Sep. 7, 2001, and which is also a continuation-in-part of U.S. Ser. No. 09/936,094, filed Sep. 7, 2001, which is a continuation of international application PCT/US2000/06001, filed Mar. 8, 2000, the disclosures of all of which are incorporated herein by reference.

FIELD OF INVENTION

The present invention is directed to drug delivery molecules that have a targeting moiety, a routing moiety and a bioactive molecule (BAM), wherein the targeting moiety significantly binds to a receptor on the surface of a cell. Binding of the targeting moiety to the receptor does not elicit a significant agonistic effect; however, it results in an uptake of the drug delivery molecule into the cell. The routing moiety is suitably coupled to the bioactive molecule, and the targeting moiety may be coupled either to the routing moiety or to the bioactive molecule. The bioactive molecule may be one that is cell-destructive, or it may be one that is useful in gene therapy. Methods and compositions drawn to particular target cells, uses, receptors, and drug delivery molecules are described in co-pending application U.S. Ser. No. 09/428,675 filed Oct. 27, 1999, which is incorporated herein by reference, and Ser. No. 09/936,094. Various alternative target cells, uses, receptors, and drug delivery molecules are contemplated beyond these disclosures. In general, all cells that express somatostatin receptor type 2 (i.e. SSR-2) are considered to be particularly suitable target cells for use in conjunction with the teachings presented herein. This definition is intended to expressly include regular (i.e. healthy) cells as well as diseased cells expressing and presenting the SSR-2. Healthy cells which express present SSR-2 include epithelial cells, smooth muscle cells, neuronal and neuroendocrine cells. Of these, certain epithelial cells that are particularly contemplated are such cells of the gastrointestinal (GI) tract, liver epithelia (parenchyma), and bile duct epithelia. As used herein, the term "gastro-intestinal tract" refers to the section of the alimentary tract located aborally from the esophageal/gastral fusion, i.e., the region beginning with the fundus of the stomach and ending with the anal portion of the rectum. Also, included under this definition are the abdominal organs, i.e. liver and pancreas, that are connected to the alimentary tract by large secretory ducts. Additional suitable target cells in the GI tract include epithelial cells lining the inner surface of the gut, and especially those lying in the strata undergoing rapid proliferation. In contrast, fibroblastic cells of the stroma and healthy endothelial cells of blood vessels are not considered to be candidates.

Especially contemplated neuroendocrine cells include glugagon-producing islet cells of the endocrine pancreas and pituitary cells having neuroendocrine characteristics. Particularly contemplated neuronal cells include peripheral somatostatinergic neurons, in particular in the cardiac atrium, and cells of the CNS (central nervous system) and PNS (peripheral nervous system) that express/present the SSR-2.

BACKGROUND OF THE INVENTION

Upon biosynthesis at the ribosomal complex, proteins undergo a series of editing steps through which proper folding and/or proper modification (e.g. by attachment of carbohydrate chains, lipid chains, or by phosphorylation) are ascertained. The editing steps occur in a stepwise manner on the surface, or within, highly specialized vesicular structures that are part of a highly dynamic network of vesicles within the cytoplasm, termed endoplasmic reticulum. In order to guide proteins through the editing processes, unique elements within the protein structure have evolved that act as sorting signals, by facilitating insertion of a given protein into membranes (a well-recognized function of attached lipid or carbohydrate residues), by defining interaction with so-called chaperones (transport molecules that move a given protein into or from a subcellular environment), or by a combination of such mechanisms. In essence, specific amino acid sequences acting as sorting signals match a given protein to its final destination where it is to exert its function, e.g. the plasma membrane for a surface receptor, the nucleus for a transcription factor, the mitochondrium for an enzyme participating in the respiratory chain. Many principles of sorting have been elucidated by the seminal studies of Blobel who was awarded the Nobel Prize for Medicine and Physiology in 2001. A large number of research groups have assembled the current knowledge about sorting signals for individual organelles (see *Trends in Biochem Sci* 16, 478-481, 1991 for an overview over nuclear translocation sequences; see Hartl and Neupert, *Science* 247, 930-938, 1990; Pfanner et al., *Annu Rev. Cell Dev. Biol.* 13, 25-51, 1997 for review of mitochondrial translocation sequences). The details of sorting are highly complex and differ with cellular environments, and most aspects of sorting, especially how multiple sub-elements of a sorting signal function, or how multiple signals for different destinations within a protein structure are assigned their order and priority of processing, are currently not understood.

In particular, the details of mitochondrial import of proteins are still unclear. The inner space of mitochondria is surrounded by two distinct membranes. Within each membrane, a designated protein complex acts as gatekeeper for macromolecules crossing the membrane. There is no "consensus sequence" of mitochondrial import signals that could act as reference for studies on structure-function-relationship. Most mitochondrial import signals are of higher complexity and are encoded by relatively long peptide sequences. After import, the signal sequence of naturally occurring proteins is cleaved off by the translocase. The recent crystal structure analysis of the enzyme importing macromolecules into the inner space of mitochondria has revealed some structural insight about the structural requirements on import sequences. Repeats of short helical structure are facilitating the translocation step proper, whereas the protein region encoding the import signal has to undergo a conformational change into a more unfolded structure to permit proteolytic cleavage off the imported protein. The sum of the individual processes of guided intracellular movements of a given macromolecule from one environment to another is often collectively referred to as "trafficking".

The invention contemplates to reduce drug toxicity and to increase drug efficacy by imparting the trafficking pathways of endogenous macromolecules upon therapeutic and imaging drugs designed to exert their function within a specific subcellular environment.

For the sake of clarity, definitions are given as follows (see also FIG. 2 and the legend to FIG. 2 in co-pending application U.S. Ser. No. 09/428,675 filed Oct. 27, 1999): A "presentation molecule" encompasses an extracellular targeting moiety, connected to an intracellular targeting moiety, termed "routing moiety", that is carrying a "bio-active molecule", or BAM.

The extracellular targeting moiety acts as a ligand (preferably a non-agonist ligand) for a transmembrane receptor that participates in internalization (a process wherein a membrane protein leaves the membrane environment, releases bound ligands to the intracellular space, and eventually returns to the membrane environment). The "routing moiety" participates in intracellular trafficking and delivers the drug molecule to a pre-determined subcellular environment. The "bioactive molecule" is the pharmacologically most active element in the composition and exerts the therapeutic effect, and/or the imaging function. In the case of a dual modality PET (SPECT)/BNCT drug, the routing moiety and the bio-active molecule are fully integrated, generating a unique drug delivery molecule (DDM). "Subcellular environment" is the collective term for all cellular organelles (such as nucleus, mitochondria, etc.), vesicular networks (such as the endoplasmatic reticulum with the Golgi apparatus), dynamically changing vesicular complexes (such as lysosomes and vesicles encountered in trafficking), and the cytoplasmic space between organelles and vesicular elements.

The use of $^{10}B$ which when subjected to epithermal neutrons decays to lithium-7 and an alpha particle is well known and has been suggested previously for destruction of cancerous cells, (see Inhibition of Human Pancreatic Cancer Growth in Nude Mice by Boron Neutron Capture Therapy, Hyyanagie, et al., *British Journal of Cancer*, 75 (5), 660-665 (1997). It is frequently referred to by the acronym BNCT. The potential efficacy of BNCT for malignant glioma is discussed in Boron Neutron Capture Therapy: Implications of Neutron Beam and Boron Compound Characteristics, F. J. Wheeler, et al., *Med. Phys.* 26 (7), 1237-1244 (July, 1999). Two articles by Y. Imahori, et al. discuss PET based BNCT using boron compound labeled with $^{18}F$, see *Clinical Cancer Research*, 4, 1825-1841 (August, 1998). U.S. patents relating to the use of BNCT include U.S. Pat. Nos. 6,074,625, 6,248,305 and 5,846,741.

In essence, BNCT employs a stable non-radioactive isotope such as boron-10 ($^{10}B$) which upon capturing a thermal neutron causes a fission reaction. In the $^{10}B$ fission, the resulting alpha and lithium particles have high energy, LET and RBE and travel less than 10 microns in tissue. As a result, selective tumor-cell killing is provided. An external beam of epithermal neutrons, with an energy maximum between 100 and 1000 eV, is employed to treat the $^{10}B$-loaded tissues by focusing upon a specific region in the body where the treatment is desired, and thus avoiding activation of the boron isotope that may have been retained in other parts of the body which may also contain the receptors being targeted. Details of reactor design and neutron beam validation are given in Wheeler et al., *Med. Phys.* 26, 1237-1244, 1999. Lee et al. in *Med. Phys.* 27, 192-202, 2000, describe a modified accelerator that is portable, more economical, and could make BNCT available for widespread hospital use. Alburger et al. in *Med. Phys.* 25, 1735-1738, 1998, have developed highly sensitive phantoms for thermal neutron depth profiling that can be used for validation of neutron beams obtained from accelerator-based BNCT facilities. In absolute numbers, a $^{10}B$ content of 5-30 ppm in tumor cells is necessary to cross the threshold for effective BNCT, corresponding to a number of about $10^9$ $^{10}B$ atoms distributed uniformly throughout a tumor cell (Fairchild and Bond, *Int. J. Radiat. Oncol. Biol. Phys.* 11, 831-840, 1985). The desirable therapeutic range between 5 and 30 microgram/g tumor tissue (Coderre and Morris, *Radiat. Res.* 151, 1-18, 1999). Subsequent calculation of tissue dosimetry has been conventionally accomplished by Monte Carlo simulations of cell destruction using estimated intracellular and extracellular concentrations of the radiopharmaceutical (Kobayashi and Kanda, *Radiation Research* 91, 77-94, 1982). The accuracy of such estimations can be substantially improved by utilization of a boron compound that is accumulating, and detectable by a second imaging modality, in a pre-determined cellular microenvironment, preferably the nucleus where neutron capture will exert the best therapeutic effect.

Monitoring and imaging of gene expression upon gene therapy has become an important procedure for validation of experimental gene therapy regimens. Most gene repair efforts have to be targeted to a specific organ, such as the liver or intestinal epithelia. Both temporal and spatial parameters of gene expression are to be assessed in living organisms in real-time mode to evaluate the effectiveness of the chosen gene delivery procedure. A variety of imaging techniques has been tested. Weissleder et al. (*Nature Medicine* 6, 351-355, 2000) describe an experimental procedure wherein a tumor made to overexpress an engineered version of the transferrin receptor could be visualized in vivo by transferrin-linked paramagnetic particles detected by MRI. However, the increase of paramagnetic particle uptake was only 2.5-fold compared to tumors not expressing the engineered receptor gene, and it was concluded by Weissleder et al. that temporal resolution was limited, and probe detection sensitivity was several orders of magnitude lower than in alternative imaging modalities, such as optical imaging and imaging of nuclear isotopes.

As alternative imaging modality, PET scanning has been tested successfully. Certain isotopes emit positively charged particles of a mass close to zero (positrons) that otherwise have the wave properties of negatively charged electrons. If a positron and an electron collide, each particle undergoes conversion into a gamma ray of 511 keV energy; since both gamma rays are emitted into opposite directions at an angle of 180 degrees, it is feasible to scan such conversion events as coinciding gamma rays in paired detectors using e.g. lutetium oxyorthosilicate as scintillation detection material, while eliminating those gamma rays that do not coincide. Details of current PET instrumentation are described in Fahey, Radiol. *Clinics North Am* 39, 919-929, 2001.

Because of high cost in running dedicated PET systems, a less expensive imaging modality (single photon emission computed tomography, SPECT, also abbreviated SPET, for single photon emission tomography) has recently gained popularity whereby a gamma ray in the energy range of 30 to 300 keV energy is emitted and detected by a modified dual-head, or multiple head, gamma camera system. SPECT imaging can be performed with isotopes of longer half-life than those used in PET, such as $^{111}In$ or $^{99m}Tc$, that are well-characterized in nuclear medicine and can be shipped from dedicated radiochemistry facilities. SPECT imaging of leukocytes labeled with $^{111}In$ or $^{99m}Tc$ has been validated as "gold standard" in detection of occult infectious and inflammatory sites (Renken et al, *Eur. J. Nucl. Med* 28, 241-252, 2001). While the use of conventional gamma camera technology is somewhat of an advantage for image acquisition, conventional SPECT does not employ electronic collimation of incoming gamma rays (Shao et al, *Phys. Med. Biol.* 42, 1965-1970, 1997), and thus is estimated to have lower sensitivity than PET by at least one order of magnitude. Multiple head detection systems and advanced image construction software are critical to achieve optimal imaging. SPECT imaging has been found to be a safe and cost-effective method with advantages over CT and other imaging methods in diagnosis and management of lung cancer patients (Goldsmith and Kostakoglu, *Radiol. Clinics North Am.* 38, 511-524, 2000). Details of current SPECT instrumentation, especially novel useful SPECT/PET hybrid detection systems, are described in Fahey, Radiol. Clinics North Am 39, 919-929, 2001.

Increasing the concentration and limiting the source of SPECT in a defined microenvironment within a target cell by pharmacological means would be a significant improvement, both for image resolution and for radiation planning by other modalities such as BNCT. It is a particular disadvantage and source of error if equal distribution of a radiation source across all cell compartments has to be assumed, rather than measuring it directly in the microenvironment that is important for the intended radiation therapy.

It has been proposed that SPECT and PET are useful to perform imaging in mouse models, with a resolution of about 1 to 2 mm and a signal collection time in the range of minutes (reviewed by Weissleder, *Nature Reviews in Cancer* 2, 2002); a mouse PET system to permit 1 mm resolution has been reported as in development by Hershman et al (*J. Neuroscience Res.* 59, 699-705, 2000). Alternative imaging modalities include the use of fluorescent reagents (Honigman et al, *Mol. Therap.* 4, 239-249, 2001) and Yang et al. *Proc Natl Acad Sci* 98, 2616-2621, 2001); the clinical use is still limited, because non-invasive detection is limited to pathological processes close to the surface, with a maximal depth of 10 cm in fluorescence-mediated tomography (Weissleder 2002).

Ray et al. have published a synopsis and a review about the application of PET to monitor gene therapy (see Table 1 in their publication in *Sem. Nucl. Med.* 31, 312-320, 2001). The best characterized model is by way of delivering a gene from Herpes Simplex virus encoding a thymidine kinase that will accept as substrate synthetic derivatives of uracil (e.g. $2'^{18}$F-2'-deoxy-1-beta-D-arabinofuranosyl-$5^{125}$I-uracil) and guanosine (e.g. $^{18}$F-ganciclovir or $^{18}$F-penciclovir), whereas the naturally occurring thymidine kinase does not. The level of gene expression to be tested is proportional to the amount of phosphorylated uracil derivative or guanosine derivative that is retained intracellularly upon phosphorylation and can be detected by PET scan. Similarly, the gene encoding somatostatin receptor type 2 has been delivered to cells to permit imaging by PET (Rogers et al., *Q J Nucl Med* 44, 208-223, 2000). This approach is still bound to the limitations of having an extracellular ligand contact a target of unknown and possibly low surface density, and cannot discriminate between cells naturally expressing the somatostatin receptor and those targeted successfully by gene therapy. Neuroendocrine tumors and gastrointestinal tissues express somatostatin type 2 receptor naturally; a tangible benefit for imaging by raising the level of somatostatin receptor further may apply to only a small subset of tumors. Furthermore, gene therapy to the liver may not be reportable at all. The Herpes virus thymidine kinase approach is far superior, because a detectable artificial intracellular substrate is enzymatically enriched only in cells that express the transgene at sufficiently high density. Still, it would be a significant improvement if the administration and overexpression of a viral enzyme interfering with energy metabolism and DNA synthesis could be avoided.

Mitochondria play a major role in the metabolism of eukaryotic cells and control pathological processes in disease and aging. For example, impaired mitochondrial function has a direct impact on ATP synthesis, regulation of intracellular $Ca^{++}$ homeostasis, generation of free radicals, and execution of programmed cell death pathways. It is therefore of great interest to target pharmaceutical compositions to mitochondria, for the purpose of monitoring physiological are pathological processes, or to deliver therapeutic drugs (see Murphy, *Trend in Biotechnol.* 15, 326-330, 1997). Specifically, tumor cells are characterized by a higher cell membrane potential and also a higher mitochondrial membrane potential (Chen, *Annu Rev. Cell Biol* 4, 155-181, 1988), permitting compounds like lipophilic cations to accumulate with a certain selectively in tumor cell mitochondria. The disruptive effect of lipophilic cations may be exerted by increase of the proton permeability of the inner membrane and inhibition of respiration (Azzone et al, *Curr. Topics Bioenerg.* 13, 1-77, 1984), or by more specific inhibitory effects e.g. on mitochondrial transcription. Lipophilic cations have been used as carriers to deliver the cytotoxic compound cisplatin to tumor cells (Steliou, U.S. Pat. No. 6,316,652). Furthermore, cation conjugates have been designed that combine to form a toxic product once inside the cancer cell mitochondrium (Rideout, *Cancer Invest* 12, 189-202, 1994).

Zhang and Haugland (U.S. Pat. No. 5,686,261) have disclosed fluorescent substituted 3'-6'-diaminoxanthenes which selectively localize in mitochondria and are retained after fixation, permeabilization, and cell death. No pharmaceutical applications are contemplated. The use of full-length bovine heart mitochondrial protein DNA sequence is suggested for creating a fusion gene with a yeast gene of interest, which upon expression will be imported into mitochondria. Herrnstadt et al. (U.S. Pat. No. 6,171,859) have disclosed methods and compositions to destroy mitochondria with defective cytochrome c oxidase in patients with Alzheimer's disease by way of a toxin conjugated to targeting molecule which is a lipophilic cation. The toxin may be a small-molecule agent or an antisense oligonucleotide. Alternatively, an imaging ligand (e.g. radioisotope suitable for PET or SPECT) may be coupled to the targeting molecule for in vivo imaging of defective mitochondria which will accumulate the imaging drug through increased membrane potential and increased levels of negatively charged phospholipids.

Because tumor cells inside of a tumor are often without significant oxygen supply, the mitochondrial membrane potential is not defined by respiration, and thus may not be optimal for uptake of lipophilic cations. Milder forms of oxygen deprivation in the periphery of tumors may elicit a stress response leading to the observed hyperpolarization of cancer cell mitochondrial and plasma membranes. Efficacious lipophilic cation uptake is thus limited to a small portion of the tumor cells. Another limitation is the access of lipophilic cations to mitochondria in normal cells which represent a pool vastly in excess over cancer cell mitochondria. Alternative modes of mitochondrial targeting are very desirable.

The use of mitochondrial import sequences instead of lipophilic cations might improve delivery of a drug to a larger population of mitochondria in a tumor, but would at the same time target mitochondria in non-tumor cells as well, thus losing a critical element of selectivity. Again, alternative modes of mitochondrial targeting are very desirable.

Somatostatin receptor ligands have been used to image cells by visualizing the level of somatostatin receptor present on the surface of a cell in a disease condition. Specific radiolabeled somatostatin analogs are disclosed in EP 607103 to visualize somatostatin receptor in primary tumors, tumor metastases, cells affected by inflammatory and autoimmune disorders, tuberculosis, and cells in organ rejection after transplantation. The use of somatostatin analogs for imaging somatostatin receptor positive cells and tissues, in particular tumors, metastases, inflammatory disorders and autoimmune disorders, is further disclosed in WO 97/01579. U.S. Pat. No. 5,976,496 discloses the use of somatostatin analogs to image atherosclerotic plaque, in particular non-critically stenotic plaque and unstable atherosclerotic plaque.

Neither of the references suggests that somatostatin analogs may be used to image angiogenesis by way of a tripartite molecule comprising a non-agonist targeting moiety, an intracellular routing moiety, and a radionucleid linked to the routing moiety. In the current invention, the somatostatin analog is not derivatized to carry a radionucleid. Neither of the references suggests using the somatostatin receptor as port of entry, translocating the imaging drug to a pre-determined subcellular microenvironment by way of sorting signals, and attaching a radiolabel to a molecular target other than a somatostatin receptor.

SUMMARY OF THE INVENTION

In one aspect of the invention, drug delivery molecules which include targeting and routing moieties, may be employed in situ for guided cell destruction. It is especially contemplated that the BAM is labeled with a label to be detected by an imaging method and carries a second cell-destructive moiety, e.g. one that will selectively destroy particular cells, as by being activated by the application of focused energy.

In a more particular aspect, it is contemplated that the drug delivery molecule (DDM) is labeled with a radionuclide suitable for PET (positron emission tomography) or for SPECT (single photon emission tomography) and includes a boron compound; this combination allows detection of the drug delivery molecule at its location in the body by PET (SPECT) and thereafter the destruction of the molecules' immediate cellular environment by the emission of radiation after capture by boron of slow neutrons which render it unstable and subject to radioactive decay.

Other examples of use of DDM include real-time monitoring of drug resistance in clinical tumors and the functional imaging of biological processes in mitochondria.

In one particular aspect, the invention provides a drug delivery molecule which comprises a bioactive molecule (BAM) of a nature to effect cell-destruction, a targeting moiety that does not activate a receptor to which it links, a routing sequence for causing delivery to an intracellular compartment in a cell having said receptor, and a label useful for imaging by Positron Emission Tomography (PET) or Single Photon Emission Tomography (SPECT).

In another particular aspect, the invention provides a drug delivery molecule which comprises a bioactive molecule (BAM), a peptide targeting moiety that does not activate a receptor to which it links, a routing sequence for causing delivery to an intracellular compartment in a cell having said receptor and a label useful for imaging by Positron Emission Tomography (PET) or Single Photon Emission Tomography (SPECT).

In another aspect of the invention, drug delivery molecules can be used to target healthy and diseased cells, and to particularly effect gene therapy by import of appropriate bioactive molecules. As used herein, the term "gene therapy" refers to any modification in expression and/or information encoded in a nucleic acid. For example, modification of expression includes up-, and down regulation of transcription and/or translation, change in chemical stability of mRNA, degree of polyadenylation, recombinant expression of homologous and/or heterologous nucleic acids, etc. Modification of information especially includes deletion, addition, transition and transversion, or recombination of nucleic acid with nucleic acid of a target cell. More particularly in this aspect, common genetic liver disorders may be addressed by means of gene therapy to correct, for example, hepatic acute porphyria (see review Grandchamp, *J. Gastroenterol. Hepatol.* 11, 1046-52 (1996), inborn errors of bile acid biosynthesis and transport (see review Balistreri, Gastroenterol. *Clin. North. Am* 28, 145-72 (1999), genetic disorders of copper and iron transport (see review Cox, *Brit. Med. Bull.* 55, 544-545, (1999), and Thalassemia and Hemophilia (see review Cahill and Colvin, *Postgraduate Med. J.* 73, 201-206 (1996). Gene therapy of such diseases may be performed by employing nucleic acid anti-sense or expression constructs as the BAM, however, various alternative BAMs may include repressors, activators, etc. Where such a drug delivery molecule comprises repressors, activators, nucleic acid anti-sense or expression constructs as the bioactive molecule, it should also be appreciated that the drug delivery molecule may be employed to modulate gene expression, for example, in liver injury and liver repair (Tracy and Fox, *Semin. Pediatr. Surg.* 5, 175-181 (1996). In addition to the treatment of liver diseases by gene therapy in this manner, treatment of genetic diseases in gastrointestinal epithelia, for example, vitamin $B_{12}$- or vitamin D malabsorption, gluten hypersensitivity, sprue, etc. is also contemplated.

In a further aspect of the invention, it is contemplated that the drug delivery molecules may also be employed to assess the gene function of genomic or other nucleic acid material in vivo. For example, the drug delivery molecule may have an EST (expressed sequence tag) expression cassette, and such drug delivery molecules are delivered in vivo to an organism. SSR-2 expressing cells will subsequently incorporate and express the EST, and a potential impact on the SSR-2 expressing cell may be observed or a new protein may be purified. Where the EST includes a regulatory element, up and down regulation of genes in SSR-2-expressing cells may be monitored or detected. An alternative procedure to detect the successful expression of the protein encoded by the EST-tagged gene introduced into the target cell is monitoring of a SPECT signal generated by a small-molecule ligand binding to the EST. This procedure is applicable in vivo and is non-invasive, avoiding the need for repeated biopsies which is particularly advantageous in the case of liver monitoring, because of the known risk of bleeding.

Another example is targeted delivery of a coding sequence for the CFTR gene, combined with a chlorine isotope used to monitor restoration of the physiological clorine channel activity after gene therapy, or a small-molecule affinity ligand for the segment of the CFTR protein to be expressed by way of the gene therapy construct introduced. This would be in contrast to the strategy favored by Brown et al (*J Bioenerg Biomembr* 29, 491-502, 1997) who proposed to influence protein folding by small molecule binding.

In a still further aspect of the invention, it is contemplated that the BAM in the drug delivery molecule may be employed to import peptides or other small molecules into a target cell, for example, to complement an intracellular biochemical or structural function of a cell, or to interrupt specific cytokines and restore gastrointestinal function in Morbus Crohn and Colitis ulcerosa. For example, restenosis of arteries after surgery may be treated by employing a drug delivery molecule having a BAM which is a cell cycle interfering agent, or which is inhibitory to a growth factor causing elimination of the growth factor receptor function).

All compositions and methods presented herein are considered suitable for use in human and veterinarian diagnosis and treatment.

DETAILED DESCRIPTION OF THE PREFERRED EMBODIMENTS

Targeting of Alternative Surface Receptors

While it is generally preferred that the targeted receptors are SSR-2 receptors, targeting of various alternative receptors is also contemplated, e.g. SSR-3 and SSR-5. For example, the SSR-3 receptor is particularly prevalent in microvascular endothelia of Kaposi Sarcoma, and the SSR-5 receptor is particularly prevalent in neuroendocrine pancreatic beta cells (e.g. an advantageous target for restoration of beta cell function). Consequently, depending upon the indication being treated, the targeting moiety of the drug delivery molecule may be a ligand that will specifically bind to one of SSR-2, SSR-3 or SSR-5. Preferred targeting moieties specific for SSR-3 and SSR-5 include molecules that are either non-agonists or antagonists. Other alternative receptors that may be targeted include the E-selectin membrane glycoprotein and the Duffy antigen/chemokine receptor, as well as the uPAR receptor, the vitronectin receptor (ÅüÆ3), the EGF receptor, the CD40, CD36, and the CD11b surface antigen.

When the SSR-2 is to be targeted, all antagonists selective for the SSR-2 are suitable as targeting moieties. Although peptides are preferred, pseudopeptides and nonpeptidic selective ligands are considered equivalents. Alternative targeting moieties include synthetic and/or natural ligands that specifically bind to a particular other receptor being targeted. For example, it is specifically contemplated that non-agonist ligands for SSR-2 may be linked to a BAM which is designed to complement known genetic defects in cystic fibrosis. A particularly preferred embodiment is a non-viral delivery vector comprising a non-agonist ligand for a surface receptor of gastrointestinal epithelia connected to a bicistronic promoter element that controls expression of the therapeutic CFTR sequence and of a monitoring sequence encoding a unique EST wherein the EST is engineered to be plasma membrane-associated and detectable by a radiolabeled plant or insect hormone, or an analog thereof.

With respect to the BAM, in an application designed for cell-destruction, it is especially contemplated that such may be an inherently toxic molecule, e.g. a peptide toxic to endothelial cells or a toxic lipid ligand for a transcription factor. For example, specific toxic peptides may include peptide fragments from the Hanta virus or from the Bax molecule (abrogating Bcl-2 mediated cell survival); a toxic lipid ligand to a transcription factor might be a modulator of PPAR activity.

Very generally, intracellular routing sequences as contemplated herein, are compounds that affect the routing of a molecule within a cell. The intracellular routing sequences are based on the seminal work of Guenter Blobel and colleagues in the field of intracellular protein topogenesis (Blobel, *Proc. Natl. Acad. Sci.* 77:1496-1500, 1980) who was awarded the Nobel Prize for his discoveries. The inclusion of a routable structural element is contemplated to overcome technical limitations of earlier concepts (e.g. Wu et al., *J. Biol. Chem.* 264:16985-16987, 1989, and related USP) where nucleic acids were rapidly degraded in lysosomes (discussion in Hart et al., *Human Gene Therapy* 9:575-585, 1998); Hart et al., *Gene Therapy* 2:552-554, 1995), or e.g. Rodwell et al., where improved peptidomimetic targeting structures cannot be selected and cannot be expressed. It is appreciated in the art that intracellular routing sequences are modular, i.e. they may be transferred to a different molecule while maintaining the operational characteristics of targeting. The relatively short and physiological routing sequence(s) encompassed herein are contemplated to have less disruptive effects on cellular secretory pathways than viral (Wagner et al., *Proc. Natl. Acad. Sci USA* 89: 7934-38, 1992) or bacterial (U.S. Pat. No. 5,643,599) sequences suggested previously. Such sequence 125 may be an oligopeptide or, preferably, a peptidomimetic connected to any bio-effective portion by any type of covalent bond. It is disclosed that intracellular routing sequences, being transferable to other protein/peptide environments, may be used as a tool of targeted drug delivery. A variety of intracellular routing sequences have been identified in different human proteins. Detailed analysis of the intracellular trafficking pathways has revealed examples that typically, a combination of several short and non-identical sequences act cooperatively. Such intracellular routing sequences include, but are not limited to: (a) cytoplasmic routing sequences, such as sequences targeting ribosomal/mRNA transportation complexes, and N-terminal or C-terminal cytoplasmic retention signals, b) ER-Golgi routing sequences, such as N- or C-terminal ER export signals, N- or C-terminal ER retention signals, N- or C-terminal ER retrieval sequences, N- or C-terminal targeting signals to the ER/intermediate Golgi compartment (ERGIC), N- or C-terminal targeting signals to cis-Golgi vesicles, N- or C-terminal targeting signals to medial Golgi vesicles, N- or C-terminal targeting sequences to trans-Golgi vesicles or to the trans-Golgi network, network export signals, trans-Golgi network retrieval sequences, and (c) N- or C-terminal nuclear translocation sequences for nuclear import, nuclear export, and nucleolar localization. Intracellular routing sequences may be further enhanced by intramolecular sequences functioning as independent elements or sub-elements that, e.g., break helical and beta sheet structures and allow C-terminal ER retention signals to work especially well (e.g. Lys-Pro).

Very generally, it is desirable to provide a DDM comprising: a BAM that is coupled to a leader that does selectively bind to a somatostatin receptor via a linkage enabler to a linker covalently connected with the leader; which linker comprises an intracellular routing or targeting sequence and a linkage enabler that is distinct from the BAM, from the intracellular targeting sequence and from the leader.

In certain preferred embodiments, the DDM is distinguished by comprising another independent structural element or sub-element that enables the necessary performance and multifunctionality of the linker-BAM connection, through the introduction of additional functional groups and residues that are contiguous to intracellular targeting sequences, but functionally unrelated to intracellular routing. A structural element with such properties is henceforth termed linkage enabler. The function of a linkage enabler is to control protection, activation and bioavailability of the BAM, and to provide attachment of a BAM to a linker at a stoichometric ratio of BAM:linker≧1, under conditions of optimized BAM-linker geometry and controlled bioavailability of the BAM. The role of the linkage enabler for the BAM is similar to the role of the intramolecular sequence element for the intracellular targeting sequences. The linkage enabler does not specifically bind to any of the intracellular transport proteins, hence does not contribute to intracellular targeting of the presentation molecule, and is functionally distinct from intracellular targeting sequences, intramolecular sequence elements, and from a combination of intracellular targeting sequences and intramolecular sequence elements. The linkage enabler may be see as an extension of the BAM, since it affects the geometric position of the BAM in the presentation molecule, and controls the bioavailability of the BAM; the linkage enabler also cooperates closely with the intramolecular sequence element which is a subelement of the linker, and may form an integrated structural and functional unit with the intramolecular sequence element.

Linkage enablers may consist of any number and kind of amino acids or residues containing isosteric functional groups. In its simplest form, a linkage enabler comprises one or more bifunctional amino acids or synthetic derivatives which are preferably connected to one or more bifunctional molecules (such as those termed "handles" in solid-phase chemistry, used for a wide array of covalent linkages) to achieve linkage to BAMs at a ratio of BAM:linkage enabler >1. All isomers, analogs and homologs of bifunctional amino acids are contemplated; for reasons of biological stability, non-amino acid derivatives are preferred. Linkage enablers are discussed in detail in my copending U.S. patent application Ser. No. 10/910,218, the disclosure of which is incorporated herein by reference. One such linkage enabler is Lys-Pro-Lys-Pro-Lys (SEQ ID NO: 35). Suitable intramolecular sequences as described therein may also be used.

Routing to Golgi Subcompartments

Both C-terminal and N-terminal signals may be utilized for routing to different Golgi subcompartments. For example, the N-terminal 27 amino acids of the glutamic acid decarboxylase isoform GAD65 function as a module to target heterologous proteins primarily to regions of the Golgi apparatus that colocalize with Lens culinaris lectin binding sites (Michele et al., *J. Cell Biol.* 126:331-341, 1994) predominantly found in the cis-Golgi compartment and the adjacent distal medial Golgi compartment (Pavelka and Ellinger, *J. Histochem. Cytochem.* 37:877-894, 1989). Thus, the GAD65 N-terminus Met-Ala-Ser-Pro-Gly-Ser-Gly-Phe-Trp-Ser-Phe-Gly-Ser-Glu-Asp-Gly-Ser-Gly-Asp-Pro-Glu-Asn-Pro-Gly-Thr-Ala-Arg (SEQ ID NO: 5), and functionally equivalent variations thereof, are contemplated as a preferred routing signal for cis-Golgi and medial Golgi subcompartment.

Routing to the trans-Golgi network may be accomplished through a Ser-X-Tyr-Gln-Arg-Leu (SEQ ID NO: 6) motif, such as the Ser-Asp-Tyr-Gln-Arg-Leu (SEQ ID NO: 7) motif in protein TGN38 (see e.g. Wang et al., *J Biol. Chem.* 268: 22853-22862, 1993) which routes the protein back into the TGN through the early endosome compartment, or through the acidic cluster motif Cys-Pro-Ser-Asp-Ser-Glu-Glu-Asp-Glu-Gly (SEQ ID NO: 8) (residue 774 to 783 in the C-terminus of the endoprotease furin; Schaefer et al., EMBO J. 14:2424-2435, 1995). Phosphorylation of the acidic cluster motif of furin (see SEQ ID NO: 24) by casein kinase II facilitates retrieval from clathrin-coated immature vesicles into the TGN by assembly protein 1. The acidic cluster motif cooperates with a second upstream sequence of the type Leu-Ile-X-Tyr-Lys-Gly-Leu (SEQ ID NO: 9) (residue 759 to 765 of furin) which comprises an imperfect leucine motif and an endocytosis motif Tyr-Lys-Gly-Leu and also binds to the assembly protein 1 complex. Targeting to the TGN may be enhanced by combining a retrieval motif such as Ser-Asp-Tyr-Gln-Arg-Leu (SEQ ID NO: 7) with a membrane-spanning sequence, such as Phe-Phe-Ala-Tyr-Leu-Val-Thr-Ala-Ala-Val-Leu-Val-Ala-Val-Leu-Tyr-Ile-Ala-Tyr from TGN38 (SEQ ID NO: 10).

Routing to different subcompartments of the Golgi apparatus may further be accomplished by using signals encoded in the transmembrane domains and certain adjacent sequences of resident Golgi proteins, such as enzymes participating in posttranslational modification by glycosylation. It is known that processing of carbohydrate side chains correlates with a distinct topology within the ER and the Golgi apparatus, such that UDG-glucuronosyltransferase can be used as a marker for ER, N-acetylgalactosamine transferase activity as a marker for late pre-Golgi/early Golgi compartments, N-acetylglucosaminyltransferase I activity as marker for the medial Golgi compartment, beta-1,4-galactosyltransferase as marker for trans-Golgi cisternae, and beta-galactoside-alpha-2,6-sialyltransferase as marker for trans-Golgi network (TGN). It has been shown that the N-terminal 33 amino acids, or the signal anchor domain, of beta-galactoside-alpha-2,6-sialyltransferase (for the human enzyme: Met-Ile-His-Thr-Asn-Leu-Lys-Lys-Lys-Phe-Ser-Cys-Cys-Val-Leu-Val-Phe-Leu-Leu-Phe-Ala-Val-Ile-Cys-Val-Trp-Glu-Lys-Lys-Gly-Ser-Tyr-Tyr-Asp; SEQ ID NO: 11), comprising the cytoplasmic domain and transmembrane domain with six C-terminally adjacent amino acids, can be transferred to replace the corresponding domains of the cell surface enzyme dipeptidyl peptidase IV, and will convert the resulting chimeric enzyme to a TGN resident protein. If the cytoplasmic sequence context of dipeptidyl transferase IV is maintained, the necessary transmembrane domain from beta-galactoside-alpha-2,6-sialyltransferase can be reduced to a routing sequence of 17 amino acids that functions as a TGN retention signal. Transmembrane domains of Golgi glycosylation-modifying enzymes are typically highly conserved among species and are distinct for each enzyme (see Wong et al., *J. Cell Biol.* 117:245-258, 1992). It is contemplated that signal anchor domains, in particular transmembrane domains with adjacent amino acids, of all resident Golgi glycosylation-modifying enzymes comprise suitable routing sequences for distinct subcompartments of the Golgi apparatus, often with narrower subcompartment selectivity than viral proteins defining viral budding regions within the Golgi apparatus. It is further contemplated that the drug delivery molecules of the invention may comprise an intracellular routing sequence derived from a transmembrane domain of a glycosylation-modifying resident Golgi enzyme.

Targeting to different Golgi subcompartments may also be achieved by using signals derived from pathogenic viruses. It is known that coronaviruses, cytomegalovirus, poliovirus, and vaccinia virus bud from the ER-intermediate Golgi compartment, whereas rubella virus buds from Golgi compartments. The budding site of a virus may not always be predictive for the routing of individual proteins; for example, the routing of rubella virus protein E1 (tubular ER exit sites/ERGIC; Hobman et al., *Mol. Biol. Cell* 9:1265-78, 1998) and the final assembly/budding of the complete virus (Golgi compartment) differ in location. The complex formation of several viral proteins, each having differing targeting motifs, within the budding virus may also restrict the repertoire of functional targeting motifs, leading to a preferred budding site more or less narrowly defined within the Golgi compartment. For example, members of the Bunyavirus family, including the Uukuniemi virus, typically bud from the Golgi, however, a very broad Golgi routing selectivity has been observed for a 81-amino acid domain from the cytoplasmic tail of the Uukuniemi G1 glycoprotein, with preference for the mid-Golgi compartment, but significant targeting to ERGIC and TGN as well (Andersson and Pettersson, *J. Virol.* 72:9585-9596, 1998). The minimum sequence with full Golgi routing capacity was defined as Thr-Trp-Lys-Ile-Ile-Lys-Pro-Phe-Trp-Trp-Ile-Leu-Ser-Leu-Leu-Cys-Arg-Thr-Cys-Ser-Lys-Arg-Leu-Asn-Arg-Ala-Glu-Arg-Leu-Lys (SEQ ID NO: 12). C-terminal Lys-Tyr-Lys-Ser-Arg-Arg-Ser-Phe-Ile-Asp-Glu-Lys-Lys-Met-Pro (SEQ ID NO: 13) is an intermediate Golgi targeting/retention signal (Lotti et al., *J. Biol. Chem.* 274:10413-10420, 1999). A partially homologous sequence can also be found in rubella virus E1 protein, as part of a larger sequence Trp-Trp-Asn-Leu-Thr-Leu-Gly-Ala-Ile-Cys-Ala-Leu-Pro-Leu-Val-Gly-Leu-Leu-Ala-Cys-Cys-Ala-Lys-Cys-Leu-Tyr-Tyr-Leu-Arg-Gly-Ala-Ile-Ala-Pro-Arg (SEQ ID NO: 14) which was identified to afford ER retention (Hobman et al., *J. Virol.* 71:7670-7680, 1997). All viral protein sequences competent to afford routing to specific Golgi subcompartments are contemplated.

Routing to Late Golgi, Post-Golgi, and Specialized Vesicles

It is thought that vesicular targeting proteins (VAMPs, SNAPs, v-SNAREs) in TGN-bound vesicles, or also in post-Golgi vesicles, bind to adaptor proteins to generate the necessary routing specificity for a given vesicle, such that reaching the appropriate destination of the vesicle is ascertained on the molecular level by recognition of a cognate resident docking receptor (syntaxin or t-SNARE). It is further contemplated that vesicular targeting, or targeting of cargo typically transported in a certain type of vesicle, may be accomplished by peptides or peptidomimetic structures interacting with resident syntaxin molecules. As an example, ER-to-TGN targeting involves the highly conserved H3 domain of syntaxin 5 with its coiled-coil motif that is sufficient for binding of vesicles. Peptidomimetic structures binding the sequence Thr-Arg-His-Ser-Glu-Ile-Ile-Lys-Leu-Glu-Asn-Ser-Ile-Arg-Glu-Leu-His-Asp-Met-Phe-Met-Asp-Met-Ala-Met (SEQ ID NO: 15) of syntaxin 1a (Kee et al., Neuron 14:991-998, 1995) are a highly preferred embodiment for docking a drug delivery molecule to the TGN compartment. It is contemplated that structures resembling the sequence 1-27 of GAD65 (SEQ ID NO: 5) may encode certain syntaxin docking capabilities, including binding to syntaxin molecules surrounding synaptic vesicles.

Lysosomal targeting from the TGN through the late endosomal compartment may be accomplished by the sequence Arg-Lys-Arg-Ser-His-Ala-Gly-Tyr-Gln-Thr-Ile (SEQ ID NO: 16) (lamp-1; Höning et al., EMBO J. 15:5230-5239, 1996 and references therein). It is specifically contemplated to target proteins involved in pathological pathways, in particular pathways of cell proliferation and cell invasiveness, for accelerated degradation in lysosomal vesicles or proteasomes. Preferred embodiments are drug delivery molecules carrying the lysosomal targeting sequence Arg-Lys-Arg-Ser-His-Ala-Gly-Tyr-Gln-Thr-Ile (SEQ ID NO: 16) or a functional equivalent fused to a peptide or peptidomimetic with high binding affinity to any of the cancer-associated or angiogenesis-associated growth factor receptors or signaling molecules. Alternatively, drug delivery molecules may carry poly-ubiquinated residues fused to a high-affinity binding moiety interacting with a growth factor or signaling molecule. Any molecule having pathophysiological significance in any disease context is contemplated.

Routing to Polarized Cellular Regions

The TGN sorting function (reviewed in Keller and Simons, J. Cell Sci. 110:3001-3009, 1997) is particularly important, because it contributes to the maintenance of plasma membrane asymmetry in polarized cells which have a barrier function and regulate macromolecular flow, such as vectorial transport, as well as compartment-specific signaling between different organ compartments. Significantly perturbed membrane polarity is a condition of cellular pathology. N-terminal basolateral sorting signals have been identified in transferrin receptor and the invariant chain of the major histocompatibility antigen class II, whereas C-terminal basolateral sorting signals have been identified in LDL receptor and lysosomal acidic phosphatase. Typically, multiple parallel sorting pathways exist. Transcytosis of a presentation molecule through endothelia may be accomplished by using one or more basolateral targeting sequences. This may be particularly useful for delivery of diverse BEMs to cell types distal to an endothelial cell overexpressing somatostatin receptors (or other surface molecules amenable to selective targeting), such as neurons under survival stress in Alzheimer's disease.

Contemplated Embodiments

Contemplated for diagnostic and therapeutic purposes are all forms of nucleolar, nuclear, and extranuclear mRNA targeting. Specifically contemplated is the use of peptidomimetic or peptidic targeting sequences mimicking any targeting structures afforded by protein complexes to target mRNA to ribosomes, including structures mimicking those afforded by Pur-alpha, staufen, and mRNA targeting complexes comprising Pur-alpha and/or staufen. Particularly preferred are targeting peptides comprising short repeats of the type Met-X-Arg or Met-X-Lys and the sequence Leu-Met-Tyr-Arg-Leu-Tyr-Met-Ala-Glu-Asp (SEQ ID NO: 17) for direct ER targeting in the context of any therapeutic intervention at a co-translational or post-translational stage, such as modulation of nascent peptide chains, co-translational delivery to the ER (or ER-ribosome complex) of a wild-type peptide fragment spanning a mutation (e.g. a mutation causing misfolding of a transmembrane coregulator protein in cystic fibrosis) whereby the wild-type fragment may participate in post-translational repair processes in the ER, and the like. The sequences Met-X-Arg, Met-X-Lys, and Leu-Met-Tyr-Arg-Leu-Tyr-Met-Ala-Glu-Asp (SEQ ID NO: 17) are further preferred for delivering to the ER modulators of the prolyl-cis-trans isomerization pathway, or of the ubiquitination pathway targeting proteins to the proteasome degradation pathway. Peptidomimetic structures of staufen and Pur-alpha are preferred over Leu-Met-Tyr-Arg-Leu-Tyr-Met-Ala-Glu-Asp (SEQ ID NO: 17) to deliver sense nucleic acid sequences to active ribosomes for repair of genetic diseases or expression of anti-apoptotic genes, or for delivery of antisense nucleic acid sequences, ribozymes, or aptamers to ER-associated ribosomes to inhibit expression of disease-associated genes of pathogenetic significance, such as growth factors and growth factor receptors, kinases and signaling molecules in cancer and pathological angiogenesis, or viral genes following infection with a hepatitis virus or an HIV virus. Preferred embodiments of drug delivery molecules are those that achieve ribozyme targeting to nucleus and cytoplasm; anti-sense nucleic acid derivative targeting to nucleus, cytoplasm and particulate ribosomes; targeting of small interfering RNA to cytoplasm.

Contemplated further is targeting of all compartments of ER and Golgi with appropriate peptidic signals and peptidomimetic derivatives thereof, e.g. to prevent or ameliorate harmful misrouting of metabolites in ER storage diseases; to interfere with sorting of oncogenes, constitutively activated kinases, growth factors and growth factor receptors in cancer; to deliver carbohydrate building blocks (lipid building blocks) in diseases linked to aberrant glycosylation (lipid metabolism); to deliver small molecules to compensate for misfolded protein species. Specifically contemplated are drug delivery molecules bearing a TGN targeting sequence linked to a branched mannosyl building block; drug delivery molecules comprising stable peptidomimetic growth factor receptor ligands as a BAM, connected to a linker bearing a TGN exit signal and a lysosomal targeting sequence, to misroute recirculating growth factor receptors in cancer cells towards a degradation pathway; drug delivery molecules comprising inhibitory substrates for PI3K or Akt as a BAM, connected to a linker bearing a lysosomal targeting sequence. The combination of TGN exit and cytoplasmic retention signals is contemplated to be particularly useful. The combination of ER exit signal and cytoplasmic retention signal defines sequential targeting action; it is contemplated that such targeting action may be functionally further improved by addition of a further signal for secretion (TGN exit) in order to perform best.

Contemplated further is routing to all compartments and pathways outside of ER and Golgi apparatus, including, but not limited to, endosomes (contemplated routing method is, e.g., by ligands to endosome-specific markers from the rab family); cell-specific synaptic and post-synaptic vesicles (contemplated method by syntaxin ligands); regions of polarity in cells (contemplated method by e.g. basolateral sorting signals); cell surface (e.g. contemplated method by modification of signals participating in endocytic transport and ER exit).

Examples of C-Terminal ER-Intermediate Golgi Compartment Routing Signals

```
                                        (SEQ ID NO: 18)
Lys-Pro-Lys-Cys-Pro-Glu-Leu-Pro-Pro-Phe-Pro-Ser-

Cys-Leu-Ser-Thr-Val-His-Phe-Ile-Ile-Phe-Val-Val-

Val-Gln-Thr-Val-Leu-Phe-Ile-Gly-Tyr-Ile-Met-Tyr-

Arg-Ser-Gln-Gln-Glu-Ala-Ala-Lys-Lys-Phe-Phe-

Ala-Ala-Ala
```

Cys-Lys-Tyr-Lys-Ser-Arg-Arg-Ser-Phe-Ile-Asp-Glu-Lys-Lys-Met-Pro (SEQ ID NO: 19) (Adenovirus E19 protein; Nilsson et al., *Cell* 58:707-718, 1989)
Lys-Tyr-Lys-Ser-Arg-Arg-Ser-Phe-Ile-Asp-Glu-Lys-Lys-Met-Pro (SEQ ID NO: 13) (Adenovirus E19 protein; Lotti et al., *J. Biol. Chem.* 274:10413-10420, 1999)
Ile-Tyr-Ile-Trp-Ala-Pro-Leu-Ala-Gly-Thr-Cys-Gly-Val-Leu-Leu-Leu-Ser-Leu-Val-Ile-Thr-Lys-Tyr-Lys-Ser-Arg-Arg-Ser-Phe-Ile-Asp-Glu-Lys-Lys-Met-Pro (SEQ ID NO: 20) fusion peptide CD8alpha-transmembrane domain/ad19 (Lotti et al., *J. Biol. Chem.* 274:10413-10420, 1999)
Lys-Tyr-Lys-Ser-Arg-Leu-Gln-Gly-Ala-Cys-Thr-Lys-Lys-Thr-Ala (SEQ ID NO: 21) HMGCoA-reductase (Jackson et al., *J. Cell Biol.* 121:317-333, 1993)
Trp-Trp-Asn-Leu-Thr-Leu-Gly-Ala-Ile-Cys-Ala-Leu-Pro-Leu-Val-Gly-Leu-Leu-Ala-Cys-Cys-Ala-Lys-Cys-Leu-Tyr-Tyr-Leu-Arg-Gly-Ala-Ile-Ala-Pro-Arg (SEQ ID NO: 14) rubella virus E1 protein (Hobman et al., *J. Virol.* 71:7670-7680, 1997)

Example of N-Terminal Cis-Golgi/Medial Golgi Compartment Routing Signal
Met-Ala-Ser-Pro-Gly-Ser-Gly-Phe-Trp-Ser-Phe-Gly-Ser-Glu-Asp-Gly-Ser-Gly-Asp-Pro-Glu-Asn-Pro-Gly-Thr-Ala-Arg (SEQ ID NO: 5) (residues 1-27 of GAD65; Michele et al., *J. Cell Biol.* 126:331-341, 1994)

Examples of C-Terminal Cis-Golgi Compartment Routing Signals

```
                                        (SEQ ID NO: 22)
Gln-Asn-Gly-Ser-Lys-Pro-Lys-Cys-Pro-Glu-Leu-Pro-

Pro-Phe-Pro-Ser-Cys-Leu-Ser-Thr-Val-His-Phe-Ile-

Ile-Phe-Val-Val-Val-Gln-Thr-Val-Leu-Phe-Ile-Gly-

Tyr-Ile-Met-Tyr-Arg-Ser-Gln-Gln-Glu-Ala-Ala-Ala (SEQ ID NO: 23)
Lys-Pro-Lys-Cys-Pro-Glu-Leu-Pro-Pro-Phe-Pro-Ser-

Cys-Leu-Ser-Thr-Val-His-Phe-Ile-Ile-Phe-Val-Val-

Val-Gln-Thr-Val-Leu-Phe-Ile-Gly-Tyr-Ile-Met-Tyr-

Arg-Ser-Gln-Gln-Glu-Ala-Ala-Ala-Lys-Ser-Phe-Tyr
```

Example of C-Terminal Medial Golgi Compartment Routing Signal
Thr-Trp-Lys-Ile-Ile-Lys-Pro-Phe-Trp-Trp-Ile-Leu-Ser-Leu-Leu-Cys-Leu-Arg-Thr-Cys-Ser-Lys-Arg-Leu-Asn-Arg-Ala-Glu-Arg-Leu-Lys (SEQ ID NO: 12) (Uukuniemi virus glycoprotein G1, cytoplasmic tail; Andersson and Pettersson, *J. Virol.* 72:9585-9596, 1998)

Examples of C-Terminal Trans-Golgi Network Routing Signals
Ser-X-Tyr-Gln-Arg-Leu (SEQ ID NO: 6)
Ser-Asp-Tyr-Gln-Arg-Leu (SEQ ID NO: 7) (human TNG protein 2/TGN38; Wang et al., *J Biol. Chem.* 268:22853-22862, 1993)
Cys-Pro-Ser-Asp-Ser-Glu-Glu-Asp-Glu-Gly (SEQ ID NO: 8) (residue 774 to 783 in the C-terminus of the endoprotease furin; Schaefer et al., *EMBO J.* 14:2424-2435, 1995).
Cys-Pro-(Phospho-Ser)-Asp-(Phospho-Ser)-Glu-Glu-Asp-Glu-Gly (SEQ ID NO: 24) (phosphorylated residue 774 to 783 C-terminal furin signal)

Example of Trans-Golgi Exit/Lysosomal Routing Signals
Arg-Lys-Arg-Ser-His-Ala-Gly-Tyr-Gln-Thr-Ile (SEQ ID NO: 16) (lamp-1; Höning et al., *EMBO J.* 15:5230-5239, 1996)

Examples of Nucleolar/Nascent Ribosome Routing Signals:
N-Terminal
Lys-Lys-Lys-His-Ser-His-Arg-Gln-Asn-Lys-Lys-Lys-Gln-Leu-Arg-Lys (SEQ ID NO: 25) (residue 24-39 of DDX10 RNA helicase)
C-Terminal
Lys-Lys-Lys-Met-Thr-Lys-Val-Ala-Glu-Ala-Lys-Lys-Val-Met-Lys-Arg (SEQ ID NO: 26) (residue 665-680 of DDX10 RNA helicase)

Example of ER-Associated Ribosome Routing Signals
Met-X-Arg (SEQ ID NO: 27); Met-X-Lys (SEQ ID NO: 28) and Leu-Met-Tyr-Arg-Leu-Tyr-Met-Ala-Glu-Asp (SEQ ID NO: 17) (human cytochrome $b_5$ (125-134); Mitoma and Ito, *EMBO J* 11:4197-4203, 1992)

Examples of Nuclear Translocation Signals
Arg-Arg-Ser-Met-Lys-Arg-Lys (SEQ ID NO: 29) (Hsieh et al., *J. Cell. Biochem.* 70: 94-109, 1998)
Pro-Lys-Lys-Lys-Arg-Lys-Val (SEQ ID NO:30) and related bipartite consensus sequences as described in Dingwall and Laskey, *Trends Biochem Sci.* 16:478-481, 1991; Yamanaka et al., *J. Biol. Chem.* 269: 21725-21734, 1994 (hereby incorporated by reference)
KKRKLIEENPKKKRKV (SEQ ID NO: 4)
and other sequences described in Jans et al., *Medicinal Research Reviews* 18:189-223, 1998 (hereby incorporated by reference).

Guided Cell Destruction by BNCT

The drug delivery molecule is particularly designed for guided cell destruction. U.S. Pat. No. 6,074,625 indicates that certain boron-containing compounds can be targeted to hormonally responsive cells containing steroid hormone receptors which are predominantly nuclear, by contacting those cells with a boron-containing agent which is conjugated to a ligand having binding specificity for the particular intercellular receptor of the cell, and it advocates using synthetic steroid analogs as ligands that are preferably anti-receptor agents or antagonists. It is also indicated that, alternatively, boron compounds can be employed for diagnosis of properties, and their locations can be determined by magnetic resonance imaging (MRI). The shortcomings of the technology presented in U.S. Pat. No. 6,074,625 are that steroid receptors are rather ubiquitous, that selective ligands have to enter target cells by diffusion, and that specific cytoplasmic binding proteins for a number of steroid hormones have been identified, thus generating a very high and long-lasting background level of boron in non-target cells. Furthermore, the additional functionality of a routing moiety to achieve improved targeting to subcellular topographies is absent in U.S. Pat. No. 6,074,625. In contrast, the current invention teaches the use of peptidic or peptidomimetic non-agonist ligands cognate to surface receptors with a restricted expression profile, and presents the advantage of target cell selectivity at the level of radiopharmaceutical uptake.

U.S. Pat. No. 5,846,741 discusses the rather cumbersome concept of tissue pre-targeting by an adaptor molecule for in vitro imaging applications prior to using BNCT to be certain that sufficient boron-10 atoms are delivered to the tumor site. The pre-targeting is carried out by administering a tagged antibody that will bind to antigens produced by or associated with the tumor cell. In a second step, an composition is administered wherein a boron-containing compound is conjugated to a molecule with high affinity for the tag existing on the previously bound antibody, causing the boron compound to be localized at the sites of the pre-treatment. As an example, the use of a known tagging pair, such as biotin and avidin, is suggested. It is also suggested that a double labeled biotin can be used, e.g. one that would carry both boron and $I^{125}$. The use of $I^{125}$ would allow one to determine that the boron compound had reached the desired tumor; moreover, monitoring could tell how long it would take for the label to be cleared from non-target organs. Disadvantages of the procedure are that the systemic use of antibodies is expensive and fraught with the risk of forming antibodies. The efficacy and selectivity of boron targeting as exemplified in U.S. Pat. No. 5,846,741 is conceptually problematic. Avidin occurs naturally in serum and will compete with a biotinylated boron composition, thereby reducing the amount of boron composition available for binding to an avidin-antibody conjugate. It is well known that cells of many abundant tissue types, e.g. skeletal muscle and intestines, contain a sizable pool of biotin. The boron-modified biotin may be taken up into that pool in the absence of a tumor-specific antibody, turning e.g. skeletal muscle (through which the neutron beam invariably has to pass on its way to the tumor) into a target for destruction. Moreover, if a biotinylated antibody is used, the boron-conjugated avidin composition is a target of proteolytic degradation, and the avidin may bind to cellular biotin on the surface of or within non-tumor tissues, again causing serious mistargeting. Since only antibodies to recirculating membrane epitopes may enter the cell, under which condition the binding tags are no longer accessible to the affinity partner in the second stage of the treatment composition, virtually all antibody-bound boron compounds will never gain entry into the target cell. Instead, they will mostly cause destruction in the extracellular space, since only one out of six possible flight directions of the alpha particle may hit the target cell, while the energy of most alpha particles is quickly absorbed by proteins and liquid in the extracellular space. Thus, it has been felt necessary to improve on the technology described in U.S. Pat. No. 5,846,741. A critical simplification enhancing targeting efficiency is felt to be the use of a single compound without antibody characteristics which entails cellular entry into predominantly tumor cells and tumor vasculature.

An article by C. S. Zuo entitled "Protron nuclear magnetic resonance measurement of p-boronophenylalanine (BPA): A therapeutic agent for boron neutron capture therapy", *Med. Phys.* 26 (7) 1230-1236, describes a need to be able to determine that the desired concentration of the B10 that has accumulated at the tumor. Generally the boron that is employed for BNCT is greater than 98% isotopically enriched in the B10 isotope which undergoes the desired fission reaction upon thermal neutron capture. Because it was so difficult to actually determine the boron concentration by NMR, instead it is suggested that proton NMR be used to detect the protons associated with the BPA carrier molecule. Although this attack is perhaps feasible, it is executed only with some difficulty. As an alternative, monitoring via neutron capture radiography (NCR) to determine when boron was carried to a tumor using BPA was advocated as a better non-invasive way of determining the concentration of boron that had reached the tumor; however, this again is not considered to be easily executed.

In alternative therapies, investigations were carried out with respect to the use of a number of radionuclides, and the possibility of using some of these nuclides for therapy and simultaneous PET diagnosis was suggested, see Stephanek et al. "Auger-Electron Spectra of Radionuclides for Therapy and Diagnostics" *Acta Oncologica,* 35 (7) 863-868, (1996). Two articles in 1999 by H. Lundqvist and M. Lubberink et al. discuss PET, see *Acta Oncologica,* 30 (3) pp. 335-341 (1999). The articles indicate that radionuclides for internal therapy usually do not emit positrons, while PET is a good tool that can be employed to obtain an accurate determination of a regional absorbed dose reaching a targeted organ of a patient. The paper suggests performing a PET investigation in advance to allow dose-planning under identical conditions that will be used in the therapy. It indicates that $^{124}I$ has an ideal half life that could be used to measure the full radioactivity integral of a commonly used therapeutic nuclide such as $^{131}I$. It is also suggested that a small amount of $^{124}I$ might be included along with $^{131}I$ to make it possible to conduct a PET study during therapy.

Whereas previously it has been necessary to employ such a dose-planning regimen where two sequential administrations are made to a patient (this approach has been used therapeutically in U.S. Pat. No. 5,846,741), applicant has now found that it is feasible to employ a combination of PET and BNCT by using a unique drug delivery molecule (DDM) wherein both the accurately detectable label and the cell-destructive molecule are simultaneously targeted to a organ or tissue. By linking the DDM to a receptor (without activating that receptor) via a selective targeting moiety, causing receptor-dependent internalization, and further causing the DDM to accumulate within a pre-determined subcellular compartment via a routing moiety, this objective can be efficiently accomplished. Then, by using PET or SPECT, it can be accurately determined whether a desired concentration has been achieved. Thereafter, assuming BNCT is being employed, a beam of thermal neutrons can be focused onto the particular organ so the boron compounds which accumulated are actuated; upon fission of the boron nuclei, cell-destructive alpha particles are created, leading to destruction of single target cells, but not of adjacent biological structures, the integrity of which may be critical to a patient's survival (e.g. major blood vessels, ureter, alveoli and acini in the lung, etc.). The benefit of this particular combination of modalities provided by applicant's invention lies in conditionally harnessing the destructive power of an alpha particle following a controlled targeting event that is monitored and validated at high resolution by a functional imaging modality. This is in contrast to the imaging modality of conventional CT, that provides information about anatomical structures without identifying those structures functionally and without having the resolution power of targeted PET (SPECT) imaging of single cell or subcellular structures, as practiced in this invention, which facilitates critical validation by identifying the desired target environment by way of its subcellular localization, and optionally by way of its functional properties.

A variety of boron compounds are well known for use in BNCT. They can be divided into mainly four groups: boronated nucleosides, boronated porphyrins, boronated amino acids, and sodium borocaptate (Lu et al., *Adv. Drug Deliv. Rev.* 26, 231-247, 1997). Examples for boronated nucleosides are beta-5-o-carboranyl-2'-deoxyuridine (Hurwitz et al., Nucleosides Nucleotides Nucleic Acids 19, 691-702, 2000) and N-3 substituted carboranyl thymidine analogs (Tjarks et al., Nucleosides Nucleotides Nucleic Acids 20, 695-698, 2001). Examples for boronated porphyrins are tetraphenyl-carborane-porphyrines and boronated protoporphyrin (BOPP). BOPP has been evaluated as a potential drug for dual BCNT and photodynamic therapy (Callahan et al, Int. J. Radiat. Oncol. Biol. Phys. 45, 761-771, 1999) and was found to accumulate in lysosomes, but not in mitochondria or the nucleus. Cellular uptake of BOPP was dependent on LDL receptor which is not a tumor-selective receptor. Consequently, the cellular selectivity and intracellular distribution of free BOPP is very unfavourable. From a synthetic and drug delivery perspective, relatively large complexes with multiple boron substitutions afford the most obvious way to introduce a maximum of boron atoms into a tumor cell. However, such complexes are typically difficult to synthesize and display considerable toxicity. Recently, bisphosphonate derivatives of dodecahydro-closo-dodecaborate have been demonstrated to have acceptable toxicity (Tjarks et al., Anticancer Res. 21, 841-846, 2001). Liposomal enclosure of o-carboranylpropylamine led to a loading density of 13,000 molecules per vesicle at acceptable toxicity, suggesting that conjugation of that compound instead of enclosure may also reduce toxicity. Borylated ferrocenium compounds are comparatively facile to synthesize and offer a high number of substituted boron atoms per molecule; however, a first series of twelve derivatives did not appreciably accumulate in tumors (Weissfloch et al., Biometals 14, 43-49, 2001). Boronated DNA-intercalating compounds, such as 5-o-carboranyl phenanthridium and 6-p-carboranyl-phenanthridium, showed limited uptake into cultured human glioma cells; low toxicity correlated with low boron accumulation (Gedda et al., Anticancer Drug Des 15, 277-286, 2000).

It is specifically contemplated that all these compounds can be covalently linked as a part of the drug delivery molecule (DDM), and applied to BNCT. The labels and a boron-containing moiety (when such is being used) may be attached independently, and preferably covalently, as a part of the drug delivery molecule at any location (i.e., at the targeting, routing, or BAM moiety). PET imaging using contemplated drug delivery molecule is desired, and the PET label is preferably attached to the routing moiety. Particularly preferred labels include tyrosine-bound $I^{123}$ and/or $I^{124}$; some of the tyrosines may be a part of or attached to the routing moiety. Where slow neutron capture is to be used to effect subsequent cell destruction, all known natural boron isotopes, as part of suitable compounds, are considered suitable for use. Such compounds may be attached as part of the drug delivery molecule by methods well known in the art. For example, borono-phenylalanine (BPA) may be linked to a routing molecule that is in turn covalently linked to a receptor-selective ligand, such as one selective for SSR-2.

While BPA is one the best characterized compounds for BNCT, it has certain disadvantages. BPA has been tested in tumor models and individual patients and found to have a tumor enrichment factor of about 3 or less, meaning that a substantial amount of boron is delivered to non-target tissues. Clinical success of BNCT seems to depend on a tumor enrichment factor of the boron compound exceeding 3 (Barth et al, Cancer 70, 2995-3007, 1992). Nguyen et al (Biochem Pharmacol. 45, 147-155, 1993) have demonstrated that BPA uptake into whole glioblastoma cells in vitro reaches its maximum after 1 h, with a cytosolic concentration of 250 ng per million of glioma cells, while concentrations in nuclei, lysosomes and microsomes were 80-fold lower, 100-fold lower, and 125-fold lower, respectively.

Improving the performance of radiopharmaceuticals for BCNT is an important need to be met. The variability in tumor enrichment of BPA observed in clinical patients by Kabalka et al (J. Nucl. Med. 38, 1762-1767, 1997) underscores the need to identify reagents with a higher and more consistent tumor enrichment factor. A different type of BNCT reagent, beta-5-o-carboranyl-2'-deoxyuridine (D-CDU) has been found to have a tumor enrichment factor in the range of 100, but showed increased accumulation in nontumor brain tissue at concentrations of 150 mg/kg (Schinazi et al, Clin. Cancer Res. 6, 725-730, 2000). The $^{10}B$ enrichment of 20% used was too low to reach therapeutically satisfactory boron concentrations and led to no significant benefit over neutron treatment alone. It remains to be determined whether higher enrichment with $^{10}B$ will allow to optimize the dosage such that a sufficient intratumoral $^{10}B$ level is maintained when less than 150 mg/kg are administered.

The relatively low tumor enrichment factor of BPA, plus the cumulative toxicity of boron compounds (Aziz et al, J. Neuropathology Exp. Neurol 59, 62-73, 2000), limits the option to improve tumor saturation by increasing the total amount of BPA administered. The broad tissue distribution of BPA-like boron compounds bears the risk of substantial tissue damage upon exposure to epithermal neutrons. Planning and performance of a suitable neutron capture treatment using fluorine-18 ($^{18}F$)-labeled BPA-like compounds thus requires optimization of a complex pharmacokinetic scenario, as described by Imahori et al (1998b), whereby the neutron radiation has to be applied during a narrow time window when washout of BPA in non-target tissue has occurred, while concurrent metabolism, decay of the short-lived $^{18}F$ isotope, and leakage of BPA from target cells still provides for an acceptable signal-to-noise ratio. Imahori et al found further that there is no similarly fast degradation, or reversal of uptake, in non-target tissues as is found in tumor cells, the level of BPA in the tumor declines within several hours to the level of BPA in healthy surrounding tissue that appears to increase. Tissue destruction and tissue repair processes, like development of inflammatory response and removal of cellular debris by macrophages, take several hours to become fully established, thus rendering unfeasible the real-time monitoring of BNCT efficacy by means of measuring the concentration of doubly-labeled $^{18}F$-$^{10}B$ free amino acid in the tumor (Imahori 1998b).

An added complication is the strict dependency of BPA enrichment on amino acid transport systems in the tumor cell plasma membrane, as observed by Imahori et al (1998b), which makes staging and grading, as well as estimates of the tumor size, prone to large errors. Thus, PET based on coupling of PET-competent radionuclids with a short half life to free amino acids is not a reliable strategy.

The current invention improves on the procedure described by Imahori et al, by pursuing an entirely different mechanistic approach to accumulate doubly-labeled PET/BNCT drugs in tumor cells, namely by receptor-mediated uptake and subsequent routing to subcellular compartments. Furthermore, it entails utilization of SPECT imaging which has not previously been suggested for monitoring BNCT, or alternatively PET-competent radionuclides with longer half-life, such as $^{64}Cu$, which will allow to observe the elimination of tumor cells through a second modality in real-time. A decisive difference in the invention, when compared to earlier disclosures, is its suitability for anti-angiogenic application of BNCT. The uptake of BPA, and numerous other BNCT drugs currently under development, depends partially on the altered membrane potential of tumor cells, and also on over expression of amino acid transporters understood as a property of tumor cells which is responsible for the observed selectivity in BNCT drug uptake.

Amino acid transporter systems are highly diverse families of membrane proteins with overlapping specificities. Three major groups have been identified: A, L, ASC (Wagner et al, *Am J Physiol Cell Physiol* 281, 1077-1093, 2001). It is a general principle that the transporters form a heterodimeric or -oligomeric complex with a heavy-chain molecule located in the plasma membrane; it is the complex that defines functionality (Pfeiffer et al, *EMBO J* 18, 49-57, 1999); much of the activity regulation in amino acid transporters appears to occur occurs post-transcriptionally (see also Freeman and Mailliard, *Biochem Biophys Res Comm* 278, 729-732, 2000 for further examples). Thus, L transporter mRNA expression by itself is not sufficiently predictive for the level of active L transporter protein in a given cell type. Systematic studies of BPA uptake and molecular types of transport proteins responsible are restricted to in-vitro studies. The closest structural analogs of BPA have been found to be transported by L system and ASC system (Samnick et al, *Nucl Med Biol* 28, 13-23, 2001), whereas BPA has been found to be transported by L system and A system (Wittig et al, *Radiat Res* 153, 173-180, 2000). While mRNA species for two molecular subtypes of the L transporter have been described in endothelia of the BBB, there is currently no agreement which subtype of L transporter is functionally dominant in BPA transport across brain endothelia of the BBB. Conflicting reports have emphasized predominance of subtype 2 (Segawa et al., *J Biol. Chem.* 274 19745-19751, 1999) or subtype 1 (Boado et al, *Proc Natl Acad Sci USA* 96, 12079-12084, 1999) in performing large neutral amino acid transport in endothelia. However, consistent with the known post-transcriptional regulation of transporter activity, functional evidence for over expression of L transporter protein in vivo has neither been found in BBB endothelia nor in tumor endothelia, based on several methodologically different studies on rat models and patient tissues. Yang et al, *Neurosurgery* 47, 189-197, 2000 describe the need to challenge the BBB with a bradykinin agonist in order to improve BPA transport into the CSF and the glioblastoma. If the L system in endothelia surrounding the tumor was substantially more activated than in nontumor tissue, or even activated to a similar degree as in glioblastoma, this step would be unnecessary. The data from Yang et al. demonstrate that in human patients, endothelia of the BBB surrounding the tumor do not overexpress any transporter (including the known L system transporter, A system transporter or ASC transporter) to a degree that selective anti-angiogenic therapy by BNCT could be practiced. In agreement with these observations, in their analysis of $^{10}$B-treated tumor tissue from patients, Imahori et al have not found BPA enrichment in endothelia, and do not teach to expect $^{10}$B in endothelia. Furthermore, in a systematic study in the Fischer rat glioblastoma model, Smith et al. (*Cancer Res.* 61, 8179-8187, 2001) have analyzed serial sections from rat tumors with conventional histology and, alternating, ion microscopy in a direct-imaging secondary ion mass spectrometer. The spatial resolution in images generated by this instrument is comparable with a high-quality light microscope, allowing imaging of individual nuclei within the tumor architecture and the architecture of surrounding tissue. Thus, it should be straightforward to identify structures resembling blood vessels that enrich $^{10}$B. However, by size, morphology, and tissue architecture, stained cells are unambiguously identifiable as tumor cells, not as microvascular endothelia. Furthermore, while perivascular edema can be assigned by topology, and be detected as space with low $^{10}$B signal, there is no enrichment of $^{10}$B in the cellular space surrounding or immediately adjacent to the edema, while tumor cells are stained distinctively (see FIG. 1 of Smith et al). These authors observe that the actively growing portion of the tumor infiltrating into surrounding tissue, while clearly detectable within 2 to 2.5 h after injection of BPA, is not maximally stained in the early phase of the BPA infusion (conventionally set to 1 to two hours, see Imahori et al). It is well known in the art that angiogenic microvessels support tumor growth by their association with the actively proliferating cell clusters, and that any imaging drug administered systemically (intravenously or otherwise) will reach interaction sites such as receptors and transporters in microvascular endothelia first, before interacting with binding sites in a tumor.

Again, the complete absence of BPA signal from vascular tissue either surrounding the tumor or penetrating the tumor, while distinctive $^{10}$B signals are observed in tumor tissue in the same area of the section, is unambiguous evidence against significant and pharmacologically useful enrichment of BPA in tumor-associated microvascular endothelia by any mechanism, including hypothetically upregulated protein levels for BPA-specific amino acid transporters, in the therapeutically relevant situation in vivo.

Last, tumor-associated endothelia are not subject to tumor-specific alterations in gene expression (e.g. they do not acquire drug resistance, or acquire tumor-specific mutations in regulatory genes such as p53); these differences extend to intracellular signaling and plasma membrane composition.

Thus, a PET/BNCT strategy targeted at tumor cells and tumor-associated microvascular endothelia is simply not suggested by the data and teachings of the Imahori et al. publications, or the other critical references in the field (see above). Hence, applicant's invention represents the first embodiment of a method to interfere with pathological antigenesis by targeted BNCT, and to monitor the impact of BNCT in real-time mode.

The possibility of destroying angiogenic tumor-associated endothelia by BCNT, as inherent in the applicant's technology, is particularly valuable, because enrichment of BPA is strikingly responsive to functional heterogeneities among tumor cell clusters within a given tumor (Imahori et al, 1998), whereas the formation of tumor vascularization does not mirror such functional microheterogeneity.

Conventional ionizing radiation would not be expected to perform destruction of tumor-associated endothelia efficiently in vivo. While microvascular endothelial cells in vitro may undergo programmed cell death within 6-10 h after exposure to ionizing radiation (Langley et al, *Brit. J. Cancer* 75, 666-672, 1997), the apoptotic response may be heterogeneous among tumors of different histologies (Meyn et al, *Int J. Radiat. Biol* 64, 583-591, 1993), thus causing only incomplete damage to the vascular supply that is unlikely to destroy the tumor.

Because the gamma radiation component used for imaging in certain contemplated embodiments of the invention is minimal, and because the thermal neutron ray may be operated in pulse mode, damage to surrounding non-tumor tissues is anticipated to be minimal in the practice of the present invention.

Pharmacological suitable concentration ranges, and modes of administration to patients, for radiotracers to be used in PET, SPECT, and BNCT, are well known in the art and may be found in the literature cited.

Monitoring Gene Expression and Gene Therapy

The invention includes methods and compositions to monitor gene expression, in particular in the context of gene therapy. The concept of mapping unknown genes by identifying unique "Expressed Sequence Tags" has been used in the Human Genome Project. Here, we refer to an EST in the literal sense as an artificially introduced heterologous first sequence (monitoring sequence) the expression of which is coupled to the expression of another second sequence (therapeutic sequence).

In one embodiment, the EST may be connected to the therapeutic gene in frame with a sequence encoding a physiological N-terminal membrane sorting signal. This approach will lead to overexpressing a therapeutic fusion protein that is physiologically sorted to the membrane (such as a surface receptor, or a regulatory membrane protein like CFTR), bearing a desired biological activity and a unique N-terminal protein tag for detection. A limitation of this approach is that the protein products of a gene therapy attempt are not always secreted, and diverting the desired gene product to a different environment may be harmful and render the intended therapeutic intervention useless. For detection of an intracellular protein, it is contemplated to introduce a radiotracer into the target cell wherein the radiotracer is attached to a composition comprising a non-agonist ligand to a surface receptor and an intracellular routing moiety delivering the radiotracer into the appropriate cellular microenvironment (a cytoplasmic routing moiety for detecting a soluble cytoplasmic protein, a nuclear routing sequence for detecting a nuclear protein, etc.).

The limitations of this strategy are that the tag may interfere with some aspect of protein function, such as complex formation with allosteric regulators, or complex formation with other proteins that participate upstream or downstream in a signal transduction pathway. Thus, in another embodiment of the invention, indirect detection of a therapeutic gene product is utilized: the EST may be expressed from a bicistronic promoter as part of a monitoring gene the product of which is sorted to the plasma membrane where it is detected by a SPECT-labeled affinity probe or ligand, whereby the bicistronic promoter will express the therapeutic gene with the same efficiency as the monitoring gene. Since the EST-containing protein is not physiologically present in plasma, or on the surface of cells that have not received the gene transfer composition, a signal after the immediate radiotracer washout period is indicative for the presence of the diagnostic EST and therefore, for successful gene expression.

The heterologous EST may originate from a plant molecule. Van der Krieken and Smit (U.S. Pat. No. 6,242,381) have disclosed chemically modified plant growth regulators that are linked to a carrier molecule for the purpose of increasing the local concentration of auxins in a plant. No application of said modified plant growth regulators outside of the plant field is contemplated by van der Krieken and Smit. Currently most preferred embodiment is a pair comprising plant auxin/auxin receptor EST, such as the known ethylene receptor.

As an example for a recognition pair consisting of a plant auxin and a plant auxin receptor, the ligand binding domain of the ethylene receptor (Schaller and Bleecker, Science 270, 1809-1811, 1995), in frame with a sequence encoding an N-terminal export signal, may be cloned as EST into a vector designed to express a therapeutic target gene from a bicistronic promoter; the auxin receptor ligand binding domain would be co-expressed at comparable level with the desired therapeutic gene, exported into the plasma membrane, and could be probed by a radiolabeled derivative of ethylene.

Contemplated for gene therapy are all cells within an organism bearing a genetic defect in the unclear portion of the genome, or in the mitochondrial portion of the genome. Particularly preferred is the delivery of the non-viral vector through a suitable and selective surface receptor to the cell of a certain cell type that physiologically expresses the gene to be repaired. In case of a secreted protein being the product of a deficient gene, the cell targeted with a gene therapy vector need not be the cell that expresses the deficient gene to be repaired.

For administration of a nucleic acid, or a nucleic acid analog, with the purpose of abrogation or downregulation of the expression of a target gene encoded in the nuclear or the mitochondrial portion of the genome, all cells bearing a suitable and selective surface receptor are contemplated wherein the downregulation of a target gene leads to the restoration of a desired cellular function (as a non-limiting example, cell survival of a neuron accumulating toxic proteins, upon interference with the expression of toxic proteins), or to the intended elimination of a pathological cell (e.g. destruction of a tumor cell). Suitable concentrations for in vivo non-viral gene therapy may vary with gene to be expressed, localization of the cell target, mode of administration. A preferred range of 1 to 60 microgram of DNA (suggested by Mixson, U.S. Pat. No. 6,080,728) may have to be modified according to specific conditions, as known in the art.

Alternatively, the heterologous EST may be a hybrid consisting of two independent ligand-binding domains (LBDs) comprising the LBD of a mutated ecdysone receptor and the LBD of a plant auxin binding protein. No prior art exists for use of ecdysone receptor as EST, or for use of insect hormone as PET imaging tracer. As an example, the insect ecdysone receptor ligand binding domain (Koelle et al, Cell 67, 59, 1991; Christiansen and Kafatos Biochem Biophys Res Comm 193, 1318, 1993; Henrik et al, Nucl. Acid Res. 18, 4143, 1990) may be cloned into a vector as described above for the ethylene receptor from the plant *Arabidopsis thaliana*, such that the receptor ligand binding domain is separated from the promoter by the export domain. Detection would be feasible with a biochemically stable radiolabeled ligand, such as ponasteron A which serves as prototype for synthetic ecdysone receptor agonists. Specifically contemplated alternative ligands include the synthetic ecdysone analogs described by Ravi et al., J. Chem. Inf. Comput. Sci. 41, 1587-1604, 2001. Further contemplated alternative ligands include the bisacylhydrazine analogs described by Smagghe et al., Insect. Biochem. Mol. Biol. 32, 187-192, 2002. Particularly preferred embodiments are a recognition pair consisting of the ligand binding domain of a newly discovered G protein-coupled receptor responsive to ecdysone-like ligands (Park et al., Proc. Natl. Acad. Sci. USA 99, 11423-11428, 2002), or a pair consisting of one out of the ecdysone-metabolizing enzymes well known in the art, or catalytically impaired mutants thereof, and ponasterone A. Further contemplated embodiments include the pair allatostatin/allatostatin receptor (Secher et al, J. Biol. Chem. 276, 47052-47060, 2001), and the pair adipokinetic hormone/adipokinetic hormone receptor (Staubli et al., Proc. Natl. Acad. Sci. USA 99, 3446-3451, 2002), and the pair bursicone/bursicone receptor (Baker and Truman, J. Exp. Biol. 205, 2555-2565, 2002).

As an alternative embodiment, a detection pair consisting of juvenile hormone and receptors for juvenile hormone (Palli et al, Proc. Natl. Acad. Sci. USA 87, 796-800, 1990), or as a specifically preferred embodiment, a detection pair consisting of juvenile hormone and juvenile hormone esterase (Hinton and Hammock, Insect Biochem Mol Biol 32, 57-66, 2001) is contemplated.

Evans et al. (U.S. Pat. No. 6,333,318) have disclosed the use of ecdysone receptor in conjunction with a co-receptor as a means to control gene expression in heterologous cells and organisms by a small molecule ligand. Evans et al. do not contemplate the use of the ecdysone receptor ligand binding domain as an EST to quantify gene expression by a radiolabeled ecdysone analog. Hogness et al. (U.S. Pat. No. 6,245, 531) have disclosed the use of a nucleotide sequence coding for an ecdysone binding domain. Hogness et al. do not contemplate the use of mutated ecdysone receptor ligand binding domain as EST, or the use of a hybrid gene with reduced hybridization specificity.

Functional Imaging of Multidrug Resistance

Functional imaging of multidrug resistance has been performed in patients with a variety of tumors, using $^{99m}$Tc sestamibi [hexakis (2-methoxy-isobutylisonitrile)-technetium (I)] which is a substrate of two drug efflux pumps, P-glycoprotein and multidrug-resistance-associated protein. (see for review Hendrikse et al, *Eur. J Nucl. Med.* 26, 283-293, 1999). Certain limitations have been identified in the use of sestamibi, such as unpredictable tumor accumulation (Dimitrakopoulou-Strauss et al, *Eur. J Nucl. Med.* 22, 434-442, 1995), rapid metabolism in the liver, and problems with the interpretation of a popular parameter in nuclear medicine, the washout rate. The washout rate from necrotic lung tumors, regardless of drug efflux pump status, may be prone to false-positive signals mimicking particularly high efflux pump activity (Kostakoglu et al, *J Nucl Med* 39, 228-234, 1998). Because multidrug resistance is a multifactorial phenomenon, it would be highly advantageous to improve current imaging technologies by using more defined efflux pump substrates with a higher specificity for individual components of multidrug resistance pathways. Furthermore, the chemical characteristics of sestamibi and related compounds are that of a lipophilic cation which is known to cross membranes depending on the degree of membrane polarization, and to accumulate in mitochondria. Thus, uptake and redistribution of sestamibi are controlled by complex parameters that are likely to vary substantially among patients and tumor types. It is apparent that the invention presented herein places the uptake of an imaging agent under control of a measurable parameter, the density of a surface receptor such as SSR-2 receptor, and accounts for enrichment in a subcellular environment that can be pre-determined by the choice of the routing moiety. Measuring activity of an individual type of drug efflux pump before, concurrent with, and after administration of a BAM reducing the expression and activity of genes encoding proteins regulating drug efflux is a further improvement over currently existing methods that attempt to monitor the drug efflux pump functionality. The decreased clearance of the radioligand from the tumor can be monitored by measuring the PET or SPECT signal intensity over time in the ROI, and can directly be correlated with the kinetics of reduced gene expression of the mdr gene of interest. Furthermore, for the purpose of reversing the multidrug resistance phenotype of the tumor, the invention is suitable to deliver into the cytoplasm blocking agents for drug efflux pumps of a size that is unlikely to permit rapid clearance by any member of the drug efflux pump families, It is predicted that the targeted/routed application of efflux pump blockers will improve the chances for a response to conventional chemotherapy, e.g. by mitoxantrone, beyond the disappointing level seen in patients who had received oral verapamil (Hendrick et al, *Ann. Oncol.* 2, 71-72, 1991) or cyclosporin A as adjuvants (Rodenburg et al, *Ann. Oncol.* 2, 305-306, 1991)

Functional Imaging of Biological Processes in Mitochondria

Steliou (U.S. Pat. No. 6,316,652) has disclosed a targeted drug agent consisting of a highly soluble cisplatin derivative, a lipophilic cation composition, and a second mitochondrial targetor compound, such as carnitine or a carnitine analog, that render the targeted drug agent susceptible to transport through the mitochondrial membrane via the L-carnitine acylcarnitine translocase system. The targeted drug agent is contemplated for therapeutic and imaging applications. U.S. Pat. No. 6,316,652 lacks the additional selection principle for a surface receptor with selectivity for pathological cells that is embodied in applicant's invention. Owing to the lack of selectivity for pathologically proliferating microvascular endothelia, the use for antiangiogenic therapy, or for imaging of pathological angiogenesis, is not contemplated. No experimental evidence is presented whether the composition will have significant selectivity for tumor mitochondria in vivo, while showing minimal accumulation into mitochondria of non-tumorous cells. Wallace and Brown (U.S. Pat. No. 5,670, 320) contemplate encoding the sequence of a mitochondrial targeting peptide in a gene therapy vector, to facilitate import of a replacement peptide for the mitochondrial ND6 protein deficient in patients with Leber's Hereditary Optic Neuropathy. Imaging of mitochondrial gene defect(s) by PET or SPECT is not disclosed. Muzyczka et al. (U.S. Pat. No. 6,020, 192) describe the use of targeting green fluorescent protein and its variants to mitochondria by means of an N-terminal targeting sequence. An 18 mer peptide is given as example. Bandman et al. (U.S. Pat. No. 6,432,915) disclose the sequence of a human mitochondrial chaperone protein HMt-GrpE and contemplate the use of portions and fragments in therapeutic and diagnostic compositions.

Inherited and acquired mitochondrial dysfunction has been recognized as an important mechanistic principle in diseases affecting the liver and other organ systems (Treem and Sokol, *Semin. Liver Dis.* 18, 237-253, 1998). Hepatic failure or chronic liver dysfunction can develop into a life-threatening condition; however, diagnosis of mitochondrial dysfunction may be difficult with currently available tools. It is thus desirable to have expanded imaging capabilities of intact and healthy mitochondria, and of real-time measurements of heteroplamsic mitochondria fraction vs. homoplasmic fraction. Prior art based on lipophiliccations as targeting elements carries the risk of introducing a bias into imaging signals, in that mitochondrial access of the imaging drug is facilitated if the mitochondria are functionally impaired or part of a diseased cell type. Moreover, prior art using targeting peptides did not contemplate a combination of a targeting moiety, a routing moiety directed to a substrate for a mitochondrial pathway and a radionuclide for PET or SPECT imaging In another preferred embodiment of the invention, the routing sequence may be a mitochondrial import peptide modeled after the mutated mitochondrial aldehyde dehydrogenase signal peptide LRAALSTARRLSRLL (SEQ ID NO: 1) (Thornton et al, *J. Biol. Chem* 268, 19906-19914, 1993) are used as a part of such a DDM. Alternative embodiments include the presequence peptide of mammalian hsp60 MLRLPTVL-RQMRPVSRALAPHLTRAYC (SEQ ID NO: 2) (Haucke et al, *J Biol. Chem* 270, 5565-5570, 1995), the cytochrome oxidase subunit IV LSLRQSIRFFKPATRTLCSSR(SEQ ID NO: 3) (Endo et al, *J Biochem.* 106, 396-400, 1989), and sequences and sequence elements reviewed in Hartl and Neupert, *Science* 247, 930-938 (1990) and Pfanner et al., *Annu Rev. Cell Dev. biol.* 13, 25-51, 1997). Another preferred routing sequence is Lys-Lys-Arg-Lys-Leu-Ile-Glu-Glu-Asn-Pro-Lys-Lys-Lys-Arg-Lys-Val (SEQ ID NO: 4). A presently preferred targeting sequence is DPhe-Cys-Phe-DTrp-Lys-Thr-Apa-Cys-Thr (cyclized by Cys-Cys bridge).

For the purpose of detecting mitochondrial deficiencies with the potential to develop into life-threatening dysfunctions (e.g. uremia and hyperammonemia), a preferred embodiment of the DDM may include a BAM which is a substrate of any of the enzymes on the respiratory chain. An alternative embodiment is as substrate for the very-long chain acyl-CoA dehydrogenase EC 1.3.99.13 linked to sudden death in childhood (Strauss et al, *Proc Natl Acad Sci USA* 92, 10496 10500, 1995); another embodiment is one that is aimed at diagnosis and treatment of congenital urea cycle disorders resulting in acute hyperammonemia (most recently reviewed in Felipo and Butterworth, *Neurochem Int.* 40, 487-491, 2002) and comprises a substrate of alpha ketoglutarate dehydrogenase and an antagonist of the NMDA receptor.

Early non-invasive diagnosis of beginning organ failure with highly predictive value is a much-needed improvement in intensive care medicine.

Improvements over Somatostatin-Agonists with Limited Receptor Selectivity

It should further be pointed out that toxicity has been observed with radiolabeled octreotide (*Nucl. Med. Comm.* 21, 97-102, 2000) as well as with unlabeled octreotide. Generally, octreotide causes delay in carbohydrate absorption and glucose production by the liver. While most patients with acromegalia treated with octreotide seem to have no adverse effects on glucose tolerance, in some cases, hypoglycemia has been found, which was explained by octreotide causing an imbalance between insulin-mediated and growth hormone-mediated blood glucose regulation (Popovic et al., *Digestion* 54(*Suppl* 1), 104-106, 1993). Up to 20% of patients develop diarrhea, and in one patient collective gastritis with subsequent decline in vitamin B12 absorption has been reported Plockiner et al, *J. Clin. Endocrinol. Metab.* 71, 1658-1662, 1990). By far the most serious side effect of octreotide is the combination of reduction in bile flow in humans (Gullo et al., *Dig. Dis. Sci.* 31, 1345-1350, 1986; Magnusson et al., *Gastroenterology* 96, 206-212, 1989) and gall bladder contractility. The reduction of gall bladder contractility in response to a meal was connected by several groups of investigators to the reduction, if not inhibition, of cholecystokinine levels in the plasma of octreotide-treated patients (see e.g. van Lissum et al., *J. Clin. Endocrinol. Metab.* 69, 557-562, 1989). The increased incidence of gallstones in response to octreotide treatment was reviewed by Dowling et al., *Digestion* 54(*Suppl* 1), 107-120, 1993. It was concluded that the timing of meals and subcutaneous octreotide injections necessary for reducing the gall bladder side effects was impractical and would defeat the whole purpose of octreotide treatment in acromegalia. The same conclusion holds for cancer patients where an infusion of octreotide might be necessary to achieve the higher doses needed; under conditions of infusion, Dowling et al reported a continuous inhibition of the cholecystokinine response. There is an urgently felt need to improve somatostatin analogs by reducing the cholestatic and metabolic side effects.

Recently, a novel synthetic cyclic analog of somatostatin, P829, (Vallabhajosula et al., *J. Nucl. Med.* 37, 1016-1022, 1996) has been introduced as depreotide into clinical evaluation for 99m-Tc-SPECT scanning of lung cancer and neuroendocrine tumors. In pre-clinical investigation, 99m-Tc-depreotide demonstrated high affinity binding to the SSR subtypes 3, 5, and 2 (Virgolini et al, *Cancer Res.* 58, 1850-1859, 1998). However, the free peptide has an apparent affinity to the ssr subtypes present in rat pancreas carcinoma membranes that is one order of magnitude lower than the affinity of octreotide (Vallahabjosula et al.), whereas the radiolabeled peptide shows higher affinity. It is a concern that modifications of the radiotracer in vivo may alter receptor affinity substantially, introduce radiotracer populations with different affinities, and generate ambiguity in image interpretation. In contrast to findings with octreotide, discrepancies in the scintigraphic results were seen in one third of neuroendocrine tumor patients treated with lanreotide (Virgolini et al, *Q J Nucl Med.* 45, 153-159, 2001) which resembles depreotide in having similar affinities to receptor subtypes. In comparison to octreotide, receptor selectivity of depreotide is not narrowed, but widened, opening depreotide to the same risk of serious side effects that has been recognized as causing a need for further improvement. It should be emphasized that none of the references on depreotide teaches the use of non-agonists in combination with an intracellular routing moiety.

The technology of the applicant improves on the prior art by avoiding the known side effects of activating the SSR-2, and setting a novel paradigm of functional imaging of a wide array of intracellular processes, by delivering radiotracers to pre-determined subcellular microenvironments selectively in cell populations characterized by expressing a receptor of interest. Furthermore, the technology extends the biological half-life of the imaging drug at the desired target site, improving safety by reducing the amount of radioactivity needed, improving imaging performance by permitting repeated and multiple scans from the same dose of radiotracer administered. The technology expands diagnostic options for somatostatin-based analogs to tumor angiogenesis, macular degeneration, and a variety of other angiogenic disorders. Applicant has come to the conclusion that the use of non-agonists, conventionally considered worthless in therapy, will overcome the serious limitations of octreotide and other SSR agonists disclosed in prior art Applicant has further demonstrated that the delivery of a non-agonist ligand is feasible in vivo and in vitro. While it is known in the art that somatostatin does not enter the nucleus, a composition comprising a non-agonist ligand and a nuclear routing moiety has been shown by the applicant to enter the nucleus. Therefore, somatostatin receptor-dependent targeting could be rendered useful for pharmacological modulation of processes in the nucleus.

An example of one DDM with a potential for anti-apoptotic gene therapy includes a selective SSTR2-ligand Pro-cyclo[Cys-Lys-Asn-Asu-Phe-D-betaMeTrp-Lys-Abu-Tyr-Ser-Ser-Cys]-Lys that is designed to deliver the sequence to a specific group of target cells, such as microvascular endothelia in Alzheimer's Disease. The SSTR2-selective ligand is connected to an N-terminal nuclear routing signal Arg-Arg-Ser-Met-Lys-Arg-Lys (SEQ ID NO: 31) contiguous to an integrated linkage enabler Pro-Orn-Pro-Orn-Pro-Orn-Asp-$NH_2$ (SEQ ID NO: 32) and a second modified C-terminal nuclear routing signal Pro-Lys-Lys-Lys-Arg-Lys-Val-Asp (SEQ ID NO: 33) that branches off the second Orn residue of the linkage enabler. Such a linkage enabler further comprises an aspartic acid-aminoguanine substituent to which the 5' end of the desired vector DNA is covalently coupled. The 3' end of the DNA terminates in another aminoguanine which is coupled to Pro-Orn-Pro-Orn (SEQ ID NO: 34) connected to the carboxy terminus of the second nuclear routing signal. The DNA sequence comprises a minimal vWF promoter that is specific for endothelial gene expression followed by the coding sequence for heme oxygenase I.

The facility of the invention has been demonstrated by the successful targeting of tumor cells in culture by SSR-2 non-agonist ligands linked to a nuclear routing moiety and a marker dye. Such has shown enrichment of that marker dye in the nucleus, by a factor of 30 or more, 48 h after application of the compound. Moreover, confocal imaging has shown very high levels SSR-2 expression in proliferating microvascular endothelia surrounding human glioblastoma, illustrating the usefulness of a DDM incorporating an SSR-2 ligand. In addition, confocal image of successful targeting of SSR-non-agonists to tumor and endothelial nuclei in a xenograft mouse model for advanced prostate cancer. When tested in a xenograft mouse model for advanced prostate cancer, only nuclei of tumor cells and angiogenic endothelial cells were found labeled 24 h after application of the SSR-2 non-agonist compound.

It can thus be seen that, the current invention overcomes the limitations in enrichment and target selectivity presented by current BCNT drugs such as BPA, and by further entailing PET (SPECT) capabilities, provides a means to validate and quantify the desired localization and concentration of the BCNT drug before treatment, and to monitor the loss of tumor cells (e.g. scored as signal reduction due to loss of detectable tumor nuclei) immediately after treatment.

Although the invention has been described with regard to its preferred embodiments, which constitute the best mode presently known to the inventor, it should be understood that various changes and modifications as would be obvious to one having the ordinary skill in this art may be made without departing from the scope of the invention which is set forth in the claims appended hereto. The disclosures of all U.S. patents and publications mentioned hereinbefore are expressly incorporated by reference.

The invention claimed is:

1. A drug delivery molecule which comprises
   a. a bioactive molecule (BAM) which includes a nucleic acid designed to effect gene therapy for cancer or for treating mitochondrial dysfunction and an expressed sequence tag (EST) which comprises nucleic acid encoding a ligand-binding element from a plant auxin binding protein, or an insect hormone binding protein,
   b. a targeting moiety which is either of cycloDPhe-Cys-Phe-DTrp-Lys-Thr-Apa-Cys-Thr, where Apa is aminopentanoic acid or Pro-cyclo[Cys-Lys-Asn-Asu-Phe-D-betaMeTrp-Lys-Abu-Tyr-Ser-Ser-Cys]-Lys that does not activate a targeted receptor to which it links, and
   c. a routing sequence for causing delivery to a subcellular compartment in a cell having said targeted receptor, which is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, and SEQ ID NO:33.

2. The molecule of claim 1 wherein said targeted receptor is a somatostatin Type 2 receptor.

3. The molecule of claim 2 wherein the BAM includes a boron isotope that will capture a slow neutron, decay and release cell-destructive radiation.

4. The molecule of claim 1 wherein the routing sequence is a mitochondrial import moiety or a nuclear translocation moiety selected from the group consisting of SEQ ID NO:1, SEQ ID NO:2, SEQ ID NO:3, SEQ ID NO:4, SEQ ID NO:29, SEQ ID NO:30, SEQ ID NO:31 and SEQ ID NO:33.

5. The molecule of claim 4 wherein the BAM includes a substrate of the mitochondrial L-carnitine acylcarnitine translocase system and a substrate of a metabolic pathway comprising either very-long chain acyl COA dehydrogenase or alpha-ketoglutarate dehydrogenase.

6. The molecule of claim 1 wherein the routing sequence is selected from the group consisting of SEQ ID NO:1; SEQ ID NO:2; SEQ ID NO:3; and SEQ ID NO:4.

7. A non-viral gene delivery vector comprising the molecule of claim 1.

8. A method of delivering the vector of claim 7 to a cell or living organism, including a human patient, and monitoring the expression of the therapeutic nucleic acid, which method comprises
   first administering the vector to the living organism;
   then, after the first delivery, administering a ligand to a plant auxin binding protein or to an insect hormone binding protein, which ligand is combined with a label useful for imaging by Positron Emission Tomography (PET), Magnetic Resonance Imaging (MRI) or single Photon Emission Computed Tomography (SPECT); and
   then detecting and quantifying the presence of the EST by scanning and processing PET, MRI or SPECT signals emitted from the label.

9. A drug delivery molecule which comprises
   a. a bioactive molecule (BAM) that includes an expressed sequence tag (EST) encoding a ligand-binding element from a plant auxin binding protein, or from an insect hormone binding protein, linked to a nucleic acid sequence complementary to a kinase desired to be reduced in expression selected from the group consisting of PI3K and Akt,
   b. a targeting moiety selected from the group consisting of cycloDPhe-Cys-Phe-DTrp-Lys-Thr-Apa-Cys-Thr; and Pro-cyclo[Cys-Lys-Asn-Asu-Phe-D-betaMeTrp-Lys-Abu-Tyr-Ser-Ser-Cys]-Lys that does not activate a targeted receptor to which it links, and
   c. a routing sequence for causing delivery to a subcellular compartment in a cell having said targeted receptor, which is selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, and SEQ ID NO:33.

10. The molecule of claim 9 wherein the targeted receptor is a somatostatin Type 2 receptor.

11. The molecule of claim 9 wherein the routing sequence is a mitochondrial import moiety or a nuclear translocation moiety selected from the group consisting of SEQ ID NO:1, SEQ ID NO:2, SEQ ID NO:3, SEQ ID NO:4, SEQ ID NO:29, SEQ ID NO:30, SEQ ID NO:31 and SEQ ID NO:33.

12. The molecule of claim 9 wherein the routing sequence is selected from the group consisting of SEQ ID NO:1; SEQ ID NO:2; SEQ ID NO:3; and SEQ ID NO:4.

13. A non-viral gene delivery vector comprising the molecule of claim 9.

14. A method of delivering the non-viral vector of claim 13 to a cell or living organism, including a human patient, and monitoring the reduction in expression of the desired gene, which comprises
   first administering the vector to the cell or living organism,
   then administering a ligand to a plant auxin binding protein or to an insect hormone binding protein, which ligand is combined with a label useful for imaging by Positron Emission Tomography (PET), Magnetic Resonance Imaging (MRI) or Single Photon Emission Computed Tomography (SPECT), and then detecting and quantifying the time-dependent reduction of the EST by way of scanning and processing PET, MRI or SPECT signals emitted from the label.

15. A drug delivery molecule which comprises the combination of:

a. a bioactive molecule (BAM) including a nucleic acid designed to effect gene therapy, which nucleic acid encodes a constitutively activated kinase, a growth factor or a growth factor receptor and an expressed sequence tag (EST) which comprises nucleic acid encoding a ligand-binding domain from the plant auxin binding protein ecdysone, b. DPhe-Cys-Phe-DTrp-Lys-Thr-Apa-Cys-Thr (cyclized by Cys-Cys bridge) where Apa is aminopentanoic acid as a targeting moiety that does not activate the SSR-2 receptor, and c. SEQ ID NO:4 as a routing sequence for causing delivery to a subcellular compartment in a cell having said targeted receptor.

16. The molecule of claim 15 wherein the BAM includes a boron isotope that will capture a slow neutron, decay and release cell-destructive radiation.

17. The molecule of claim 15 wherein the BAM includes a substrate of the mitochondrial L-carnitine acylcarnitine translocase system and a substrate of a metabolic pathway comprising either very-long chain acyl COA dehydrogenase or alpha-ketoglutarate dehydrogenase.

18. A non-viral gene delivery vector comprising the molecule of claim 15.

19. A method of delivering the vector of claim 18 to a cell or living organism, including a human patient, and monitoring the expression of the therapeutic nucleic acid, which method comprises first administering the vector to the cell or living organism;

then, after the first delivery, administering a ligand to a plant auxin binding protein, which ligand is combined with a label useful for imaging by Positron Emission Tomography (PET), Magnetic Resonance Imaging (MRI) or single Photon Emission Computed Tomography (SPECT); and then detecting and quantifying the presence of the EST by scanning and processing PET, MRI or SPECT signals emitted from the label.

* * * * *

```
                           SEQUENCE LISTING

<160> NUMBER OF SEQ IDS NOS: 35

<210> SEQ ID NO 1
  <211> LENGTH: 15
  <212> TYPE: PRT
  <213> ORGANISM: Homo sapiens

<400> SEQUENCE: 1

Leu Arg Ala Ala Leu Ser Thr Ala Arg Arg Leu Ser Arg Leu Leu
  1               5                   10                  15

<210> SEQ ID NO 2
  <211> LENGTH: 27
  <212> TYPE: PRT
  <213> ORGANISM: Homo sapiens

<400> SEQUENCE: 2

Met Leu Arg Leu Pro Thr Val Leu Arg Gln Met Arg Pro Val Ser Arg
  1               5                   10                  15

Ala Leu Ala Pro His Leu Thr Arg Ala Tyr Cys
              20                  25

<210> SEQ ID NO 3
  <211> LENGTH: 21
  <212> TYPE: PRT
  <213> ORGANISM: Homo sapiens

<400> SEQUENCE: 3

Leu Ser Leu Arg Gln Ser Ile Arg Phe Phe Lys Pro Ala Thr Arg Thr
  1               5                   10                  15

Leu Cys Ser Ser Arg
              20

<210> SEQ ID NO 4
  <211> LENGTH: 16
  <212> TYPE: PRT
  <213> ORGANISM: Homo sapiens

<400> SEQUENCE: 4

Lys Lys Arg Lys Leu Ile Glu Glu Asn Pro Lys Lys Arg Lys Val
  1               5                   10                  15

<210> SEQ ID NO 5
  <211> LENGTH: 27
  <212> TYPE: PRT
  <213> ORGANISM: Homo sapiens

<400> SEQUENCE: 5

Met Ala Ser Pro Gly Ser Gly Phe Trp Ser Phe Gly Ser Gln Asp Gly
  1               5                   10                  15

Ser Gly Asp Pro Glu Asn Pro Gly Thr Ala Arg
              20                  25
```

```
<210> SEQ ID NO 6
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 6

Ser Xaa Tyr Gln Arg Leu
1               5

<210> SEQ ID NO 7
<211> LENGTH: 5
<212> TYPE: PRT
<213> ORGANISM: Homo sapiens

<400> SEQUENCE: 7

Ser Asp Tyr Gln Arg
1               5

<210> SEQ ID NO 8
<211> LENGTH: 10
<212> TYPE: PRT
<213> ORGANISM: Homo sapiens

<400> SEQUENCE: 8

Cys Pro Ser Asp Ser Glu Glu Asp Glu Gly
1               5                   10

<210> SEQ ID NO 9
<211> LENGTH: 7
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 9

Leu Ile Xaa Tyr Lys Gly Leu
1               5

<210> SEQ ID NO 10
<211> LENGTH: 19
<212> TYPE: PRT
<213> ORGANISM: Homo sapiens

<400> SEQUENCE: 10

Phe Phe Ala Tyr Leu Val Thr Ala Ala Val Leu Val Ala Val Leu Tyr
1               5                   10                  15

Ile Ala Tyr

<210> SEQ ID NO 11
<211> LENGTH: 34
<212> TYPE: PRT
<213> ORGANISM: Homo sapiens

<400> SEQUENCE: 11

Met Ile His Thr Asn Leu Lys Lys Lys Phe Ser Cys Cys Val Leu Val
1               5                   10                  15

Phe Leu Leu Phe Ala Val Ile Cys Val Trp Glu Lys Lys Gly Ser Tyr
            20                  25                  30

Tyr Asp
```

```
<210> SEQ ID NO 12
<211> LENGTH: 30
<212> TYPE: PRT
<213> ORGANISM: Homo sapiens

<400> SEQUENCE: 12

Thr Trp Lys Ile Ile Lys Pro Phe Trp Trp Ile Leu Ser Leu Leu Cys
1               5                   10                  15

Arg Thr Cys Ser Lys Arg Leu Asn Arg Ala Glu Arg Leu Lys
            20                  25                  30

<210> SEQ ID NO 13
<211> LENGTH: 15
<212> TYPE: PRT
<213> ORGANISM: Homo sapiens

<400> SEQUENCE: 13

Lys Tyr Lys Ser Arg Arg Ser Phe Ile Asp Glu Lys Lys Met Pro
1               5                   10                  15

<210> SEQ ID NO 14
<211> LENGTH: 35
<212> TYPE: PRT
<213> ORGANISM: Homo sapiens

<400> SEQUENCE: 14

Trp Trp Asn Leu Thr Leu Gly Ala Ile Cys Ala Leu Pro Leu Val Gly
1               5                   10                  15

Leu Leu Ala Cys Cys Ala Lys Cys Leu Tyr Tyr Leu Arg Gly Ala Ile
            20                  25                  30

Ala Pro Arg
        35

<210> SEQ ID NO 15
<211> LENGTH: 25
<212> TYPE: PRT
<213> ORGANISM: Homo sapiens

<400> SEQUENCE: 15

Thr Arg His Ser Glu Ile Ile Lys Leu Glu Asn Ser Ile Arg Glu Leu
1               5                   10                  15

His Asp Met Phe Met Asp Met Ala Met
            20                  25

<210> SEQ ID NO 16
<211> LENGTH: 11
<212> TYPE: PRT
<213> ORGANISM: Homo sapiens

<400> SEQUENCE: 16

Arg Lys Arg Ser His Ala Gly Tyr Gln Thr Ile
1               5                   10

<210> SEQ ID NO 17
<211> LENGTH: 10
<212> TYPE: PRT
<213> ORGANISM: Homo sapiens

<400> SEQUENCE: 17

Leu Met Tyr Arg Leu Tyr Met Ala Glu Asp
1               5                   10
```

-continued

```
<210> SEQ ID NO 18
<211> LENGTH: 51
<212> TYPE: PRT
<213> ORGANISM: Homo sapiens

<400> SEQUENCE: 18

Lys Pro Lys Cys Pro Glu Leu Pro Pro Phe Pro Ser Cys Leu Ser Thr
1               5                   10                  15

Val His Phe Ile Ile Phe Val Val Gln Thr Val Leu Phe Ile Gly
            20                  25                  30

Tyr Ile Met Tyr Arg Ser Gln Gln Glu Ala Ala Ala Lys Lys Phe Phe
        35                  40                  45

Ala Ala Ala
    50

<210> SEQ ID NO 19
<211> LENGTH: 16
<212> TYPE: PRT
<213> ORGANISM: Homo sapiens

<400> SEQUENCE: 19

Cys Lys Tyr Lys Ser Arg Arg Ser Phe Ile Asp Glu Lys Met Pro
1               5                   10                  15

<210> SEQ ID NO 20
<211> LENGTH: 36
<212> TYPE: PRT
<213> ORGANISM: Homo sapiens

<400> SEQUENCE: 20

Ile Tyr Ile Trp Ala Pro Leu Ala Gly Thr Cys Gly Val Leu Leu Leu
1               5                   10                  15

Ser Leu Val Ile Thr Lys Tyr Lys Ser Arg Arg Ser Phe Ile Asp Glu
            20                  25                  30

Lys Lys Met Pro
        35

<210> SEQ ID NO 21
<211> LENGTH: 15
<212> TYPE: PRT
<213> ORGANISM: Homo sapiens

<400> SEQUENCE: 21

Lys Tyr Lys Ser Arg Leu Gln Gly Ala Cys Thr Lys Lys Thr Ala
1               5                   10                  15

<210> SEQ ID NO 22
<211> LENGTH: 48
<212> TYPE: PRT
<213> ORGANISM: Homo sapiens

<400> SEQUENCE: 22

Gln Asn Gly Ser Lys Pro Lys Cys Pro Glu Leu Pro Pro Phe Pro Ser
1               5                   10                  15

Cys Leu Ser Thr Val His Phe Ile Phe Val Val Gln Thr Val
            20                  25                  30

Leu Phe Ile Gly Tyr Ile Met Tyr Arg Ser Gln Gln Glu Ala Ala Ala
        35                  40                  45

<210> SEQ ID NO 23
<211> LENGTH: 48
<212> TYPE: PRT
<213> ORGANISM: Homo sapiens
```

```
<400> SEQUENCE: 23

Lys Pro Lys Cys Pro Glu Leu Pro Pro Phe Pro Ser Cys Leu Ser Thr
1               5                   10                  15

Val His Phe Ile Ile Phe Val Val Gln Thr Val Leu Phe Ile Gly
            20                  25                  30

Tyr Ile Met Tyr Arg Ser Gln Gln Glu Ala Ala Ala Lys Ser Phe Tyr
            35                  40                  45

<210> SEQ ID NO 24
<211> LENGTH: 5
<212> TYPE: PRT
<213> ORGANISM: Homo sapiens

<400> SEQUENCE: 24

Glu Glu Asp Glu Gly
1               5

<210> SEQ ID NO 25
<211> LENGTH: 16
<212> TYPE: PRT
<213> ORGANISM: Homo sapiens

<400> SEQUENCE: 25

Lys Lys Lys His Ser His Arg Gln Asn Lys Lys Gln Leu Arg Lys
1               5                   10                  15

<210> SEQ ID NO 26
<211> LENGTH: 16
<212> TYPE: PRT
<213> ORGANISM: Homo sapiens

<400> SEQUENCE: 26

Lys Lys Lys Met Thr Lys Val Ala Glu Ala Lys Lys Val Met Lys Arg
1               5                   10                  15

<210> SEQ ID NO 27
<211> LENGTH: 3
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 27

Met Xaa Arg
1

<210> SEQ ID NO 28
<211> LENGTH: 3
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid

<400> SEQUENCE: 28

Met Xaa Lys
1

<210> SEQ ID NO 29
<211> LENGTH: 7
<212> TYPE: PRT
<213> ORGANISM: Homo sapiens
```

```
<400> SEQUENCE: 29

Arg Arg Ser Met Lys Arg Lys
1               5

<210> SEQ ID NO 30
<211> LENGTH: 7
<212> TYPE: PRT
<213> ORGANISM: Homo sapiens

<400> SEQUENCE: 30

Pro Lys Lys Lys Arg Lys Val
1               5

<210> SEQ ID NO 31
<211> LENGTH: 7
<212> TYPE: PRT
<213> ORGANISM: Homo sapiens

<400> SEQUENCE: 31

Arg Arg Ser Met Lys Arg Lys
1               5

<210> SEQ ID NO 32
<211> LENGTH: 7
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa is Ornithine
<220> FEATURE:
<221> NAME/KEY: MISC_FEATURE
<222> LOCATION: (4)..(4)
<223> OTHER INFORMATION: Xaa is Ornithine
<220> FEATURE:
<221> NAME/KEY: misc_feature
<222> LOCATION: (6)..(6)
<223> OTHER INFORMATION: Xaa is Ornithine

<400> SEQUENCE: 32

Pro Xaa Pro Xaa Pro Xaa Asp
1               5

<210> SEQ ID NO 33
<211> LENGTH: 8
<212> TYPE: PRT
<213> ORGANISM: Homo sapiens

<400> SEQUENCE: 33

Pro Lys Lys Lys Arg Lys Val Asp
1               5

<210> SEQ ID NO 34
<211> LENGTH: 4
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa is Ornithine
<220> FEATURE:
<221> NAME/KEY: MISC_FEATURE
<222> LOCATION: (4)..(4)
<223> OTHER INFORMATION: Xaa is Ornithine

<400> SEQUENCE: 34

Pro Xaa Pro Xaa
1
```

```
<210> SEQ ID NO 35
<211> LENGTH: 5
<212> TYPE: PRT
<213> ORGANISM: Homo sapiens

<400> SEQUENCE: 35

Lys Pro Lys Pro Lys
1               5
```